United States Patent
Davidson et al.

(10) Patent No.: US 9,540,659 B2
(45) Date of Patent: Jan. 10, 2017

(54) MODIFIED ADENO-ASSOCIATED VIRUS VECTOR COMPOSITIONS

(71) Applicant: UNIVERSITY OF IOWA RESEARCH FOUNDATION, Iowa City, IA (US)

(72) Inventors: Beverly L. Davidson, Iowa City, IA (US); Maria Scheel, Iowa City, IA (US); Ryan Boudreau, Iowa City, IA (US); Alejandro Mas Monteys, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/410,983

(22) PCT Filed: Mar. 14, 2013

(86) PCT No.: PCT/US2013/031644
§ 371 (c)(1),
(2) Date: Dec. 23, 2014

(87) PCT Pub. No.: WO2014/007858
PCT Pub. Date: Jan. 9, 2014

(65) Prior Publication Data
US 2015/0184197 A1  Jul. 2, 2015

Related U.S. Application Data

(60) Provisional application No. 61/668,839, filed on Jul. 6, 2012.

(51) Int. Cl.
| | | |
|---|---|---|
| C07H 21/04 | (2006.01) | |
| C12N 15/11 | (2006.01) | |
| C12N 15/63 | (2006.01) | |
| C12N 15/864 | (2006.01) | |
| C12N 15/86 | (2006.01) | |

(52) U.S. Cl.
CPC ..... *C12N 15/86* (2013.01); *C12N 2750/14141* (2013.01); *C12N 2750/14143* (2013.01); *C12N 2830/38* (2013.01)

(58) Field of Classification Search
CPC .............. C12N 15/86; C12N 2750/14141; C12N 2830/38
USPC ...................... 536/24.2; 435/320.1
See application file for complete search history.

(56) References Cited

U.S. PATENT DOCUMENTS

| | | | |
|---|---|---|---|
| 5,139,941 A | 8/1992 | Muzyczka | |
| 7,132,277 B1 * | 11/2006 | Bett et al. | 435/320.1 |
| 2002/0194630 A1 | 12/2002 | Manning et al. | |
| 2006/0063174 A1 | 3/2006 | Turner et al. | |

FOREIGN PATENT DOCUMENTS

| | | |
|---|---|---|
| WO | 9961034 A1 | 12/1999 |
| WO | 2011133874 A1 | 10/2011 |
| WO | 2012109667 A1 | 8/2012 |

OTHER PUBLICATIONS

Wu et al. (2009) Mol. Ther., vol. 18 (1), pp. 80-86.*
Barcia et al. (2007) Mol. Ther., vol. 15(12), 2154-2163.*
Dong et al., "Characterization of Genome Integrity for Oversized Recombinant AAV Vector", Molecular Therapy vol. 18 (1), 87-92 (2010).
GenBank AC005516.1; Nov. 21, 1998; 47 pages, retrieved from http://www.ncbi.nlm.nih.gov/nuccore/ac005516 on May 19, 2013.
Govindasamy et al., "Structurally Mapping the Diverse Phenotype of Adeno-Associated Virus Serotype 4", J. Vir. 80 (23), 11556-11570 (2006).
Patent Cooperation Treaty, International Searching Authority, Search Report and Written Opinion for PCT/US2013/031644, 11 pages, Jun. 5, 2013.
Chen et al., "Molecular signatures of disease brain endothelia provide new sites for CNS-directed enzyme therapy", Nature Medicine vol. 15 (10), 1215-1218 (2009).
Chen et al., "Sialic acid deposition impairs the utility of AAV9, but not peptide-modified AAVs for brain gene therapy in a mouse model of lysosomal storage disease", Molecular Therapy. 20 (7), 1393-1399 (2012).
Grimm et al., "Adeno-Associated Virus Vectors for Short Hairpin RNA Expression", Methods in Enzymology, vol. 392, 381-405 (2005).
Kota et al., "Therapeutic microRNA Delivery Suppresses Tumorigenesis in a Murine Liver Cancer Model", Cell, vol. 137 (6), 1005-1017 (2009).

* cited by examiner

*Primary Examiner* — Anne Marie S Wehbe
(74) *Attorney, Agent, or Firm* — Viksnins Harris & Padys PLLP

(57) ABSTRACT

An adeno-associated virus filler component comprising a nucleic acid of between 3300 and 4200 nucleotides in length is disclosed.

18 Claims, 32 Drawing Sheets

Figure 2A (SEQ ID NO: 3)

Sequence: 5pFBAAVmU6miHDS1stuffer Assembly Range: 1 to 9110

```
>5'_GTVC_G0202
|
        10        20        30        40        50
TTCGCTTTCTTCCCTTCCTTTCTCGCCACGTTCGCCGGCTTTCCCCGTCA
AAGCGAAAGAAGGGAAGGAAAGAGCGGTGCAAGCGGCCGAAAGGGCAGT 60        70        80        90       100
AGCTCTAAATCGGGGGCTCCCTTTAGGGTTCCGATTTAGTGCTTTACGGC
TCGAGATTTAGCCCCCGAGGGAAATCCCAAGGCTAAATCACGAAATGCCG 110       120       130       140       150
ACCTCGACCCCAAAAAACTTGATTAGGGTGATGGTTCACGTAGTGGGCCA
TGGAGCTGGGGTTTTTGAACTAATCCCACTACCAAGTGCATCACCCGGT 160       170       180       190       200
TCGCCCTGATAGACGGTTTTTCGCCCTTTGACGTTGGAGTCCACGTTCTT
AGCGGGACTATCTGCCAAAAAGCGGGAAACTGCAACCTCAGGTGCAAGAA 210       220       230       240       250
AATAGTGGACTCTTGTTCCAAACTGGAACAACACTCAACCCTATCTCGGT
TTATCACCTGAGAACAAGGTTTGACCTTGTTGTGAGTTGGGATAGAGCCA 260       270       280       290       300
CTATTCTTTTGATTTATAAGGGATTTTGCCGATTTCGGCCTATTGGTTAA
GATAAGAAAACTAAATATTCCCTAAAACGGCTAAAGCCGGATAACCAATT 310       320       330       340       350
AAAATGAGCTGATTTAACAAAAATTTAACGCGAATTTTAACAAAATATTA
TTTTACTCGACTAAATTGTTTTTAAATTGCGCTTAAAATTGTTTTATAAT 360       370       380       390       400
ACGCTTACAATTTAGGTGGCACTTTTCGGGGAAATGTGCGCGGAACCCCT
TGCGAATGTTAAATCCACCGTGAAAAGCCCCTTTACACGCGCCTTGGGGA 410       420       430       440       450
ATTTGTTTATTTTTCTAAATACATTCAAATATGTATCCGCTCATGAGACA
TAAACAAATAAAAAGATTTATGTAAGTTTATACATAGGCGAGTACTCTGT

>Beta-lactamase
                                        |
       460       470       480       490 |     500
ATAACCCTGATAAATGCTTCAATAATATTGAAAAAGGAAGAGTATGAGTA
TATTGGGACTATTTACGAAGTTATTATAACTTTTTCCTTCTCATACTCAT
```

Figure 2B

```
              510         520         530         540         550
      TTCAACATTTCCGTGTCGCCCTTATTCCCTTTTTTGCGGCATTTTGCCTT
      AAGTTGTAAAGGCACAGCGGGAATAAGGGAAAAAACGCCGTAAAACGGAA 560         570         580         590         600
      CCTGTTTTTGCTCACCCAGAAACGCTGGTGAAAGTAAAAGATGCTGAAGA
      GGACAAAAACGAGTGGGTCTTTGCGACCACTTTCATTTTCTACGACTTCT 610         620         630         640         650
      TCAGTTGGGTGCACGAGTGGGTTACATCGAACTGGATCTCAACAGCGGTA
      AGTCAACCCACGTGCTCACCCAATGTAGCTTGACCTAGAGTTGTCGCCAT 660         670         680         690         700
      AGATCCTTGAGAGTTTTCGCCCCGAAGAACGTTTTCCAATGATGAGCACT
      TCTAGGAACTCTCAAAAGCGGGGCTTCTTGCAAAAGGTTACTACTCGTGA 710         720         730         740         750
      TTTAAAGTTCTGCTATGTGGCGCGGTATTATCCCGTATTGACGCCGGGCA
      AAATTTCAAGACGATACACCGCGCCATAATAGGGCATAACTGCGGCCCGT 760         770         780         790         800
      AGAGCAACTCGGTCGCCGCATACACTATTCTCAGAATGACTTGGTTGAGT
      TCTCGTTGAGCCAGCGGCGTATGTGATAAGAGTCTTACTGAACCAACTCA 810         820         830         840         850
      ACTCACCAGTCACAGAAAAGCATCTTACGGATGGCATGACAGTAAGAGAA
      TGAGTGGTCAGTGTCTTTTCGTAGAATGCCTACCGTACTGTCATTCTCTT 860         870         880         890         900
      TTATGCAGTGCTGCCATAACCATGAGTGATAACACTGCGGCCAACTTACT
      AATACGTCACGACGGTATTGGTACTCACTATTGTGACGCCGGTTGAATGA 910         920         930         940         950
      TCTGACAACGATCGGAGGACCGAAGGAGCTAACCGCTTTTTTGCACAACA
      AGACTGTTGCTAGCCTCCTGGCTTCCTCGATTGGCGAAAAAACGTGTTGT 960         970         980         990        1000
      TGGGGGATCATGTAACTCGCCTTGATCGTTGGGAACCGGAGCTGAATGAA
      ACCCCCTAGTACATTGAGCGGAACTAGCAACCCTTGGCCTCGACTTACTT 1010        1020        1030        1040        1050
      GCCATACCAAACGACGAGCGTGACACCACGATGCCTGTAGCAATGGCAAC
      CGGTATGGTTTGCTGCTCGCACTGTGGTGCTACGGACATCGTTACCGTTG
```

Figure 2C

```
          1060       1070       1080       1090       1100
     AACGTTGCGCAAACTATTAACTGGCGAACTACTTACTCTAGCTTCCCGGC
     TTGCAACGCGTTTGATAATTGACCGCTTGATGAATGAGATCGAAGGGCCG 1110       1120       1130       1140       1150
     AACAATTAATAGACTGGATGGAGGCGGATAAAGTTGCAGGACCACTTCTG
     TTGTTAATTATCTGACCTACCTCCGCCTATTTCAACGTCCTGGTGAAGAC 1160       1170       1180       1190       1200
     CGCTCGGCCCTTCCGGCTGGCTGGTTTATTGCTGATAAATCTGGAGCCGG
     GCGAGCCGGGAAGGCCGACCGACCAAATAACGACTATTTAGACCTCGGCC 1210       1220       1230       1240       1250
     TGAGCGTGGGTCTCGCGGTATCATTGCAGCACTGGGGCCAGATGGTAAGC
     ACTCGCACCCAGAGCGCCATAGTAACGTCGTGACCCCGGTCTACCATTCG 1260       1270       1280       1290       1300
     CCTCCCGTATCGTAGTTATCTACACGACGGGGAGTCAGGCAACTATGGAT
     GGAGGGCATAGCATCAATAGATGTGCTGCCCCTCAGTCCGTTGATACCTA 1310       1320       1330       1340       1350
     GAACGAAATAGACAGATCGCTGAGATAGGTGCCTCACTGATTAAGCATTG
     CTTGCTTTATCTGTCTAGCGACTCTATCCACGGAGTGACTAATTCGTAAC 1360       1370       1380       1390       1400
     GTAACTGTCAGACCAAGTTTACTCATATATACTTTAGATTGATTTAAAAC
     CATTGACAGTCTGGTTCAAATGAGTATATATGAAATCTAACTAAATTTTG 1410       1420       1430       1440       1450
     TTCATTTTTAATTTAAAAGGATCTAGGTGAAGATCCTTTTTGATAATCTC
     AAGTAAAAATTAAATTTTCCTAGATCCACTTCTAGGAAAAACTATTAGAG 1460       1470       1480       1490       1500
     ATGACCAAAATCCCTTAACGTGAGTTTTCGTTCCACTGAGCGTCAGACCC
     TACTGGTTTTAGGGAATTGCACTCAAAAGCAAGGTGACTCGCAGTCTGGG 1510       1520       1530       1540       1550
     CGTAGAAAGATCAAAGGATCTTCTTGAGATCCTTTTTTTCTGCGCGTAA
     GCATCTTTTCTAGTTTCCTAGAAGAACTCTAGGAAAAAAGACGCGCATT 1560       1570       1580       1590       1600
     TCTGCTGCTTGCAAACAAAAAAACCACCGCTACCAGCGGTGGTTTGTTTG
     AGACGACGAACGTTTGTTTTTTGGTGGCGATGGTCGCCACCAAACAAAC
```

Figure 2D

```
             1610       1620       1630       1640       1650
         CCGGATCAAGAGCTACCAACTCTTTTTCCGAAGGTAACTGGCTTCAGCAG
         GGCCTAGTTCTCGATGGTTGAGAAAAAGGCTTCCATTGACCGAAGTCGTC 1660       1670       1680       1690       1700
         AGCGCAGATACCAAATACTGTTCTTCTAGTGTAGCCGTAGTTAGGCCACC
         TCGCGTCTATGGTTTATGACAAGAAGATCACATCGGCATCAATCCGGTGG 1710       1720       1730       1740       1750
         ACTTCAAGAACTCTGTAGCACCGCCTACATACCTCGCTCTGCTAATCCTG
         TGAAGTTCTTGAGACATCGTGGCGGATGTATGGAGCGAGACGATTAGGAC 1760       1770       1780       1790       1800
         TTACCAGTGGCTGCTGCCAGTGGCGATAAGTCGTGTCTTACCGGGTTGGA
         AATGGTCACCGACGACGGTCACCGCTATTCAGCACAGAATGGCCCAACCT 1810       1820       1830       1840       1850
         CTCAAGACGATAGTTACCGGATAAGGCGCAGCGGTCGGGCTGAACGGGGG
         GAGTTCTGCTATCAATGGCCTATTCCGCGTCGCCAGCCCGACTTGCCCCC 1860       1870       1880       1890       1900
         GTTCGTGCACACAGCCCAGCTTGGAGCGAACGACCTACACCGAACTGAGA
         CAAGCACGTGTGTCGGGTCGAACCTCGCTTGCTGGATGTGGCTTGACTCT 1910       1920       1930       1940       1950
         TACCTACAGCGTGAGCTATGAGAAAGCGCCACGCTTCCCGAAGGGAGAAA
         ATGGATGTCGCACTCGATACTCTTTCGCGGTGCGAAGGGCTTCCCTCTTT 1960       1970       1980       1990       2000
         GGCGGACAGGTATCCGGTAAGCGGCAGGGTCGGAACAGGAGAGCGCACGA
         CCGCCTGTCCATAGGCCATTCGCCGTCCCAGCCTTGTCCTCTCGCGTGCT 2010       2020       2030       2040       2050
         GGGAGCTTCCAGGGGGAAACGCCTGGTATCTTTATAGTCCTGTCGGGTTT
         CCCTCGAAGGTCCCCCTTTGCGGACCATAGAAATATCAGGACAGCCCAAA 2060       2070       2080       2090       2100
         CGCCACCTCTGACTTGAGCGTCGATTTTTGTGATGCTCGTCAGGGGGGCG
         GCGGTGGAGACTGAACTCGCAGCTAAAAACACTACGAGCAGTCCCCCGC 2110       2120       2130       2140       2150
         GAGCCTATGGAAAAACGCCAGCAACGCGGCCTTTTTACGGTTCCTGGCCT
         CTCGGATACCTTTTTGCGGTCGTTGCGCCGGAAAAATGCCAAGGACCGGA
```

Figure 2E

```
            2160       2170       2180       2190       2200
    TTTGCTGGCCTTTTGCTCACATGTTCTTTCCTGCGTTATCCCCTGATTCT
    AAACGACCGGAAAACGAGTGTACAAGAAAGGACGCAATAGGGGACTAAGA 2210       2220       2230       2240       2250
    GTGGATAACCGTATTACCGCCTTTGAGTGAGCTGATACCGCTCGCCGCAG
    CACCTATTGGCATAATGGCGGAAACTCACTCGACTATGGCGAGCGGCGTC 2260       2270       2280       2290       2300
    CCGAACGACCGAGCGCAGCGAGTCAGTGAGCGAGGAAGCGGAAGAGCGCC
    GGCTTGCTGGCTCGCGTCGCTCAGTCACTCGCTCCTTCGCCTTCTCGCGG 2310       2320       2330       2340       2350
    TGATGCGGTATTTTCTCCTTACGCATCTGTGCGGTATTTCACACCGCATA
    ACTACGCCATAAAAGAGGAATGCGTAGACACGCCATAAAGTGTGGCGTAT 2360       2370       2380       2390       2400
    GACCAGCCGCGTAACCTGGCAAAATCGGTTACGGTTGAGTAATAAATGGA
    CTGGTCGGCGCATTGGACCGTTTTAGCCAATGCCAACTCATTATTTACCT

>Tn7R_8-10-11
                         |
            2410       2420       2430       2440       2450
    TGCCCTGCGTAAGCGGGTGTGGGCGGACAATAAAGTCTTAAACTGAACAA
    ACGGGACGCATTCGCCCACACCCGCCTGTTATTTCAGAATTTGACTTGTT 2460       2470       2480       2490       2500
    AATAGATCTAAACTATGACAATAAAGTCTTAAACTAGACAGAATAGTTGT
    TTATCTAGATTTGATACTGTTATTTCAGAATTTGATCTGTCTTATCAACA 2510       2520       2530       2540       2550
    AAACTGAAATCAGTCCAGTTATGCTGTGAAAAGCATACTGGACTTTTGT
    TTTGACTTTAGTCAGGTCAATACGACACTTTTTCGTATGACCTGAAAACA 2560       2570       2580       2590       2600
    TATGGCTAAAGCAAACTCTTCATTTTCTGAAGTGCAAATTGCCCGTCGTA
    ATACCGATTTCGTTTGAGAAGTAAAAGACTTCACGTTTAACGGGCAGCAT 2610       2620       2630       2640       2650
    TTAAAGAGGGGCGTGGCCAAGGGCATGGTAAAGACTATATTCGCGGCGTT
    AATTTCTCCCCGCACCGGTTCCCGTACCATTTCTGATATAAGCGCCGCAA 2660       2670       2680       2690       2700
    GTGACAATTTACCGAACAACTCCGCGGCCGGGAAGCCGATCTCGGCTTGA
    CACTGTTAAATGGCTTGTTGAGGCGCCGGCCCTTCGGCTAGAGCCGAACT
```

Figure 2F

```
        2710        2720        2730        2740        2750
ACGAATTGTTAGGTGGCGGTACTTGGGTCGATATCAAAGTGCATCACTTC
TGCTTAACAATCCACCGCCATGAACCCAGCTATAGTTTCACGTAGTGAAG 2760        2770        2780        2790        2800
TTCCCGTATGCCCAACTTTGTATAGAGAGCCACTGCGGGATCGTCACCGT
AAGGGCATACGGGTTGAAACATATCTCTCGGTGACGCCCTAGCAGTGGCA 2810        2820        2830        2840        2850
 AATCTGCTTGCACGTAGATCACATAAGCACCAAGCGCGTTGGCCTCATGC
 TTAGACGAACGTGCATCTAGTGTATTCGTGGTTCGCGCAACCGGAGTACG 2860        2870        2880        2890        2900
TTGAGGAGATTGATGAGCGCGGTGGCAATGCCCTGCCTCCGGTGCTCGCC
AACTCCTCTAACTACTCGCGCCACCGTTACGGGACGGAGGCCACGAGCGG 2910        2920        2930        2940        2950
GGAGACTGCGAGATCATAGATATAGATCTCACTACGCGGCTGCTCAAACT
CCTCTGACGCTCTAGTATCTATATCTAGAGTGATGCGCCGACGAGTTTGA 2960        2970        2980        2990        3000
TGGGCAGAACGTAAGCCGCGAGAGCGCCAACAACCGCTTCTTGGTCGAAG
ACCCGTCTTGCATTCGGCGCTCTCGCGGTTGTTGGCGAAGAACCAGCTTC 3010        3020        3030        3040        3050
GCAGCAAGCGCGATGAATGTCTTACTACGGAGCAAGTTCCCGAGGTAATC
CGTCGTTCGCGCTACTTACAGAATGATGCCTCGTTCAAGGGCTCCATTAG 3060        3070        3080        3090        3100
GGAGTCCGGCTGATGTTGGGAGTAGGTGGCTACGTCTCCGAACTCACGAC
CCTCAGGCCGACTACAACCCTCATCCACCGATGCAGAGGCTTGAGTGCTG 3110        3120        3130        3140        3150
CGAAAAGATCAAGAGCAGCCCGCATGGATTTGACTTGGTCAGGGCCGAGC
GCTTTTCTAGTTCTCGTCGGGCGTACCTAAACTGAACCAGTCCCGGCTCG 3160        3170        3180        3190        3200
CTACATGTGCGAATGATGCCCATACTTGAGCCACCTAACTTTGTTTTAGG
GATGTACACGCTTACTACGGGTATGAACTCGGTGGATTGAAACAAAATCC

<gentamicin
                                        |
        3210        3220        3230    3240 |   3250
GCGACTGCCCTGCTGCGTAACATCGTTGCTGCTGCGTAACATCGTTGCTG
CGCTGACGGGACGACGCATTGTAGCAACGACGACGCATTGTAGCAACGAC
```

Figure 2G

```
          3260      3270      3280      3290      3300
CTCCATAACATCAAACATCGACCCACGGCGTAACGCGCTTGCTGCTTGGA
GAGGTATTGTAGTTTGTAGCTGGGTGCCGCATTGCGCGAACGACGAACCT 3310      3320      3330      3340      3350
TGCCCGAGGCATAGACTGTACAAAAAAACAGTCATAACAAGCCATGAAAA
ACGGGCTCCGTATCTGACATGTTTTTTGTCAGTATTGTTCGGTACTTTT 3360      3370      3380      3390      3400
CCGCCACTGCGCCGTTACCACCGCTGCGTTCGGTCAAGGTTCTGGACCAG
GGCGGTGACGCGGCAATGGTGGCGACGCAAGCCAGTTCCAAGACCTGGTC 3410      3420      3430      3440      3450
TTGCGTGAGCGCATACGCTACTTGCATTACAGTTTACGAACCGAACAGGC
AACGCACTCGCGTATGCGATGAACGTAATGTCAAATGCTTGGCTTGTCCG 3460      3470      3480      3490      3500
TTATGTCAACTGGGTTCGTGCCTTCATCCGTTTCCACGGTGTGCGTCACC
AATACAGTTGACCCAAGCACGGAAGTAGGCAAAGGTGCCACACGCAGTGG 3510      3520      3530      3540      3550
CGGCAACCTTGGGCAGCAGCGAAGTCGAGGCATTTCTGTCCTGGCTGGCG
GCCGTTGGAACCCGTCGTCGCTTCAGCTCCGTAAAGACAGGACCGACCGC 3560      3570      3580      3590      3600
AACGAGCGCAAGGTTTCGGTCTCCACGCATCGTCAGGCATTGGCGGCCTT
TTGCTCGCGTTCCAAAGCCAGAGGTGCGTAGCAGTCCGTAACCGCCGGAA 3610      3620      3630      3640      3650
GCTGTTCTTCTACGGCAAGGTGCTGTGCACGGATCTGCCCTGGCTTCAGG
CGACAAGAAGATGCCGTTCCACGACACGTGCCTAGACGGGACCGAAGTCC 3660      3670      3680      3690      3700
AGATCGGAAGACCTCGGCCGTCGCGGCGCTTGCCGGTGGTGCTGACCCCG
TCTAGCCTTCTGGAGCCGGCAGCGCCGCGAACGGCCACCACGACTGGGGC 3710      3720      3730      3740      3750
GATGAAGTGGTTCGCATCCTCGGTTTTCTGGAAGGCGAGCATCGTTTGTT
CTACTTCACCAAGCGTAGGAGCCAAAAGACCTTCCGCTCGTAGCAAACAA 3760      3770      3780      3790      3800
CGCCCAGGACTCTAGCTATAGTTCTAGTGGTTGGCTACAGCTTGCATGCC
GCGGGTCCTGAGATCGATATCAAGATCACCAACCGATGTCGAACGTACGG
```

Figure 2H

```
>AAV_ITR_(94bp)
        |
     3810      3820      3830      3840      3850
TGCAGGCAGCTGCGCGCTCGCTCGCTCACTGAGGCCGCCCGGGCGTCGGG
ACGTCCGTCGACGCGCGAGCGAGCGAGTGACTCCGGCGGGCCCGCAGCCC 3860      3870      3880      3890      3900
CGACCTTTGGTCGCCCGGCCTCAGTGAGCGAGCGAGCGCGCAGAGAGGGA
GCTGGAAACCAGCGGGCCGGAGTCACTCGCTCGCTCGCGCGTCTCTCCCT 3910      3920      3930      3940      3950
GTGGCCAACTCCATCACTAGGGGTTCCTTGTAGTTAATGATTAACCCGCC
CACCGGTTGAGGTAGTGATCCCCAAGGAACATCAATTACTAATTGGGCGG

>mU6 promoter
                                        |
     3960      3970      3980      3990      4000
ATGCTACTTATCTACGTAGCCATGCTCTAGTGAATTCGACGCCGCCATCT
TACGATGAATAGATGCATCGGTACGAGATCACTTAAGCTGCGGCGGTAGA 4010      4020      4030      4040      4050
CTAGGCCCGCGCCGGCCCCCTCGCACAGACTTGTGGGAGAAGCTCGGCTA
GATCCGGGCGCGGCCGGGGGAGCGTGTCTGAACACCCTCTTCGAGCCGAT 4060      4070      4080      4090      4100
CTCCCCTGCCCCGGTTAATTTGCATATAATATTTCCTAGTAACTATAGAG
GAGGGGACGGGGCCAATTAAACGTATATTATAAAGGATCATTGATATCTC 4110      4120      4130      4140      4150
GCTTAATGTGCGATAAAAGACAGATAATCTGTTCTTTTTAATACTAGCTA
CGAATTACACGCTATTTTCTGTCTATTAGACAAGAAAAATTATGATCGAT 4160      4170      4180      4190      4200
CATTTTACATGATAGGCTTGGATTTCTATAAGAGATACAAATACTAAATT
GTAAAATGTACTATCCGAACCTAAAGATATTCTCTATGTTTATGATTTAA 4210      4220      4230      4240      4250
ATTATTTTAAAAACAGCACAAAAGGAAACTCACCCTAACTGTAAAGTAA
TAATAAAATTTTTTGTCGTGTTTTCCTTTGAGTGGGATTGACATTTCATT 4260      4270      4280      4290      4300
TTGTGTGTTTTGAGACTATAAATATCCCTTGGAGAAAAGCCTTGTTTGCG
AACACACAAAACTCTGATATTTATAGGGAACCTCTTTTCGGAACAAACGC
```

Figure 2I

```
                                       >miHDS1
                                           |
        4310       4320       4330  |   4340       4350
   TTTAGTGAACCGTCAGATGGTACCGTTTAAACTCGAGTGAGCGATGCTGG
   AAATCACTTGGCAGTCTACCATGGCAAATTTGAGCTCACTCGCTACGACC 4360       4370       4380       4390       4400
   CTCGCATGGTCGATACTGTAAAGCCACAGATGGGTGTCGACCATGCGAGC
   GAGCGTACCAGCTATGACATTTCGGTGTCTACCCACAGCTGGTACGCTCG 4410       4420       4430       4440       4450
   CAGCACCGCCTACTAGAGCGGCCGCCACAGCGGGGAGATCCAGACATGAT
   GTCGTGGCGGATGATCTCGCCGGCGGTGTCGCCCCTCTAGGTCTGTACTA

>stuffer
           |
        4460   |   4470       4480       4490       4500
   AAGATACATTTTTTGAATTCGGGCTATCCCAGGTTGCCTTGGTTCATGGC
   TTCTATGTAAAAAACTTAAGCCCGATAGGGTCCAACGGAACCAAGTACCG 4510       4520       4530       4540       4550
   AAATGGGACGTTAAGAGGGCAGAGAGAATATGAACAGAAACTGTTCTAAT
   TTTACCCTGCAATTCTCCCGTCTCTCTTATACTTGTCTTTGACAAGATTA 4560       4570       4580       4590       4600
   ATTGGTCATTTAATGTGTAAGTATTGTTCTTTTTTAAACCTCCTTCATTT
   TAACCAGTAAATTACACATTCATAACAAGAAAAATTTGGAGGAAGTAAA 4610       4620       4630       4640       4650
   TTTTTCCAGGAATTGCTGGACACAGTGGCTTGGTGTGTGTCTGAGGACTG
   AAAAAGGTCCTTAACGACCTGTGTCACCGAACCACACACAGACTCCTGAC 4660       4670       4680       4690       4700
   TAGGCCATGGCCCTAGGTTGTGGTTTTAGGTCTCAGGTGCTCTTCCTGGC
   ATCCGGTACCGGGATCCAACACCAAAATCCAGAGTCCACGAGAAGGACCG 4710       4720       4730       4740       4750
   TGTCTCCTTGCTTCTTTCCCATGTCCTCTTCTTTGTTTCCAGCCATTTCT
   ACAGAGGAACGAAGAAAGGGTACAGGAGAAGAAACAAAGGTCGGTAAAGA 4760       4770       4780       4790       4800
   CCCTTATGCTTAAGTTTGGTGCAGCAGGGTTTGGCTGCTCTCAGATTCCT
   GGGAATACGAATTCAAACCACGTCGTCCCAAACCGACGAGAGTCTAAGGA
```

Figure 2J

```
              4810        4820        4830        4840        4850
      GCTTCCTCAGATGCTGTAGTTGTCAGGCCCAGCGGGCTGGCAGCGGGATC
      CGAAGGAGTCTACGACATCAACAGTCCGGGTCGCCCGACCGTCGCCCTAG 4860        4870        4880        4890        4900
      AGGATCTGGCTAGGTTTGCTCTCACTGTGGCAGAGTAGGGGGAGGCGTGG
      TCCTAGACCGATCCAAACGAGAGTGACACCGTCTCATCCCCCTCCGCACC 4910        4920        4930        4940        4950
      GAGAGCACGTGTGACCCCAGGCCAGCTGTAGGGAGCATAGGCATGGTCAC
      CTCTCGTGCACACTGGGGTCCGGTCGACATCCCTCGTATCCGTACCAGTG 4960        4970        4980        4990        5000
      GTAGCCTTCAGGTCCTAGACTTTGTCTTCTCATGAGTATGGCTGTGTGTG
      CATCGGAAGTCCAGGATCTGAAACAGAAGAGTACTCATACCGACACACAC 5010        5020        5030        5040        5050
      TATGGTGAAAACTAGGTTCTACTTAGCCCAAGAAAATGGGCACATTTTGC
      ATACCACTTTTGATCCAAGATGAATCGGGTTCTTTTACCCGTGTAAAACG 5060        5070        5080        5090        5100
      ATGTGGTTTCTGTAGAGAAATGCACTGGGTATCTGACATAGCCTGGCAGC
      TACACCAAAGACATCTCTTTACGTGACCCATAGACTGTATCGGACCGTCG 5110        5120        5130        5140        5150
      ATGCCTCCCTCAGGTAGGTTAGTCTCAGGCGGTGAAGCACGTGTGTCCAG
      TACGGAGGGAGTCCATCCAATCAGAGTCCGCCACTTCGTGCACACAGGTC 5160        5170        5180        5190        5200
      CAAGAACTTCATATGTGGCATAAAGTCTCCGTTCTGTGAGGTGCTGGCAA
      GTTCTTGAAGTATACACCGTATTTCAGAGGCAAGACACTCCACGACCGTT 5210        5220        5230        5240        5250
      ATCACCACCACCGTCAAGAGGCTGAAGTGATTTTTGTCTAGGGAGGCAGG
      TAGTGGTGGTGGCAGTTCTCCGACTTCACTAAAAACAGATCCCTCCGTCC 5260        5270        5280        5290        5300
      AAAGGCTTCCTGGAGTCAGCAGCCAGTAGGTGAAAGAGTAGATTGGAGAC
      TTTCCGAAGGACCTCAGTCGTCGGTCATCCACTTTCTCATCTAACCTCTG 5310        5320        5330        5340        5350
      CTTCTTAATCATCACCGCCTCTTGTCTCAAGGGGTGCCAGGAAGCTGTGG
      GAAGAATTAGTAGTGGCGGAGAACAGAGTTCCCCACGGTCCTTCGACACC
```

Figure 2K

```
              5360        5370        5380        5390        5400
      AGGCTGAACCCATCTTATGCTGCCAGAGAGTGGGACACCATGAGGGTCAG
      TCCGACTTGGGTAGAATACGACGGTCTCTCACCCTGTGGTACTCCCAGTC 5410        5420        5430        5440        5450
      GTCAAGGGGTTGTACCTTGTTTGGTAGAGAATTAGGGGCTCTTGAAGACT
      CAGTTCCCCAACATGGAACAAACCATCTCTTAATCCCCGAGAACTTCTGA 5460        5470        5480        5490        5500
      TTGGATGTGGTCAGGGGAGTGTATCATTTAGGAAGAGTGACCCGGTGAGG
      AACCTACACCAGTCCCCTCACATAGTAAATCCTTCTCACTGGGCCACTCC 5510        5520        5530        5540        5550
      ACGTGGGGTAGAGGAGGACAGGTGGGAGGGAGTCCAGGTGGGAGTGAGTA
      TGCACCCCATCTCCTCCTGTCCACCCTCCCTCAGGTCCACCCTCACTCAT 5560        5570        5580        5590        5600
      GACCCAGCAGGAGTGCAGGGCCTCGAGCCAGGATGGTGGCAGGGCTGTGA
      CTGGGTCGTCCTCACGTCCCGGAGCTCGGTCCTACCACCGTCCCGACACT 5610        5620        5630        5640        5650
      GGAGAGGCAGCCACCTGTGTGTCTGCGGAAGCAGGGGCAAGAGGGAAGAG
      CCTCTCCGTCGGTGGACACACAGACGCCTTCGTCCCCGTTCTCCCTTCTC 5660        5670        5680        5690        5700
      GCCAGCAGCGTGCTGCCATCACCCAGCGACTGGCGTAGATTGTGAGAGAC
      CGGTCGTCGCACGACGGTAGTGGGTCGCTGACCGCATCTAACACTCTCTG 5710        5720        5730        5740        5750
      CATTCCCTGCTCTTAGGAGGGGCTGAGTTTTAGTTTTCTCTTGTTATACA
      GTAAGGGACGAGAATCCTCCCCGACTCAAAATCAAAGAGAACAATATGT 5760        5770        5780        5790        5800
      ATAAGCTTGGTATTTGTTTACAAAACATTTGTAAAGCTAAATCAAGGTTT
      TATTCGAACCATAAACAAATGTTTTGTAAACATTTCGATTTAGTTCCAAA 5810        5820        5830        5840        5850
      GATAAGGCTTCTAGTTTTATTTAAGAAGTAATGTTGAAATAAATGTTTGT
      CTATTCCGAAGATCAAAATAAATTCTTCATTACAACTTTATTTACAAACA 5860        5870        5880        5890        5900
      CCAATTCGCTTTGCTCATTTAAGGACTTTCAGTACAAACTGCAACAACAG
      GGTTAAGCGAAACGAGTAAATTCCTGAAAGTCATGTTTGACGTTGTTGTC
```

Figure 2L

```
         5910       5920       5930       5940       5950
GATTAGGATTTAAACGTTTCTGAGATGTTTTTACTCCTCAGAATTTCCCA
CTAATCCTAAATTTGCAAAGACTCTACAAAAATGAGGAGTCTTAAAGGGT 5960       5970       5980       5990       6000
GAATGTGATCTGGTTTTGATTTTCAAGCTTGCTGACCCAATAGGTTAACC
CTTACACTAGACCAAAACTAAAAGTTCGAACGACTGGGTTATCCAATTGG 6010       6020       6030       6040       6050
CACAAGTTTTACGAAGACCATCTCAGTCCACTTACATCAACTGCCCATGC
GTGTTCAAAATGCTTCTGGTAGAGTCAGGTGAATGTAGTTGACGGGTACG 6060       6070       6080       6090       6100
CACGGTTAAAGAGATCATCGACTGATGTTTGGCACAGCTTCCTCCCTCTT
GTGCCAATTTCTCTAGTAGCTGACTACAAACCGTGTCGAAGGAGGGAGAA 6110       6120       6130       6140       6150
GGGTGGGCAAGCATTTGGAAGAGAAGGCTCCTATGGGTGAGAGTGGGGCA
CCCACCCGTTCGTAAACCTTCTCTTCCGAGGATACCCACTCTCACCCCGT 6160       6170       6180       6190       6200
CCAAAGTCTTCCCTGTCCCATCCCCTAGCTTGAGAAGCCCTTCTCTAATG
GGTTTCAGAAGGGACAGGGTAGGGGATCGAACTCTTCGGGAAGAGATTAC 6210       6220       6230       6240       6250
TGGACTTTGTGCCGTTAGCATCGTTACTAGCTTGAAGTTGACCATCTGGA
ACCTGAAACACGGCAATCGTAGCAATGATCGAACTTCAACTGGTAGACCT 6260       6270       6280       6290       6300
CGTACTTTCTGGTTTAGCCTCACAAGTGAGCAAGGAGGGTTGAGAGATGT
GCATGAAAGACCAAATCGGAGTGTTCACTCGTTCCTCCCAACTCTCTACA 6310       6320       6330       6340       6350
GCTGTGAGGAATGTGGGGCCCCAGCTGGCAGCAGGCTCTGGGTCAGGGGG
CGACACTCCTTACACCCCGGGGTCGACCGTCGTCCGAGACCCAGTCCCCC 6360       6370       6380       6390       6400
GCAGGGACCACGGGCATACCTGACAGTGAGGAGGGTCTAGTAGGGGATCA
CGTCCCTGGTGCCCGTATGGACTGTCACTCCTCCCAGATCATCCCCTAGT 6410       6420       6430       6440       6450
GTTCCCCTGTTGTTCTTTAGAATTTTCTGGATATTCTTCTTTATTGATTT
CAAGGGGACAACAAGAAATCTTAAAAGACCTATAAGAAGAAATAACTAAA
```

Figure 2M

```
        6460       6470       6480       6490       6500
TGGGATGTGAACAATAGAATCAACTTCTACTTGTAGATTGATTTAGGGAG
ACCCTACACTTGTTATCTTAGTTGAAGATGAACATCTAACTAAATCCCTC 6510       6520       6530       6540       6550
AACTTATACCTCAGATGTTAAGTCACCCTGTCCAGAATGTGGGATGCTTT
TTGAATATGGAGTCTACAATTCAGTGGGACAGGTCTTACACCCTACGAAA 6560       6570       6580       6590       6600
CCTATTTGTTCAGAACTTTTTAAATTACCTCAGAAGCACATGAAATTTAA
GGATAAACAAGTCTTGAAAAATTTAATGGAGTCTTCGTGTACTTTAAATT 6610       6620       6630       6640       6650
AGGATTTTAAAAAAACTTAAAGATTATTTCACATAGCTCTTGCACATTT
TCCTAAAATTTTTTTTGAATTTCTAATAAAGTGTATCGAGAACGTGTAAA 6660       6670       6680       6690       6700
CTTGATAAATGAATCCTCAGGTATTCCTCTGTTTTTGTTACTAATAGTTA
GAACTATTTACTTAGGAGTCCATAAGGAGACAAAAACAATGATTATCAAT 6710       6720       6730       6740       6750
CTTCTTATGGGTTTTTTTTCCCCTGAAAATCATTTATCAAACGTATGTGG
GAAGAATACCCAAAAAAAAGGGGACTTTTAGTAAATAGTTTGCATACACC 6760       6770       6780       6790       6800
CTTATTTTCTGAAGGATGTTTGATAATTTTGGAAGATATGAAAGTCTTCA
GAATAAAAGACTTCCTACAAACTATTAAAACCTTCTATACTTTCAGAAGT 6810       6820       6830       6840       6850
TATTTTACAAGGTTTGAGGTCTCTTTAAGCTGCATGGTTCTCATGTCAGC
ATAAAATGTTCCAAACTCCAGAGAAATTCGACGTACCAAGAGTACAGTCG 6860       6870       6880       6890       6900
TCCCAAAGCAGAAGACGGCATGTTGAAAAATGCCGTAGAGAAGATACTTC
AGGGTTTCGTCTTCTGCCGTACAACTTTTACGGCATCTCTTCTATGAAG 6910       6920       6930       6940       6950
TTTTCCACCTGTTTTCAACTCATATCATCTTGAATTTCAGGGCACCTTTC
AAAAGGTGGACAAAAGTTGAGTATAGTAGAACTTAAAGTCCCGTGGAAAG 6960       6970       6980       6990       7000
CATGCTCCTAGTGCTTGCTATCTGTTTATTATTTTCCTTCCTGAATACCC
GTACGAGGATCACGAACGATAGACAAATAATAAAAGGAAGGACTTATGGG
```

Figure 2N

```
          7010       7020       7030       7040       7050
     TGAACTCCAGCATGTTCTGCTGTAATTCTGGCCTCCCTGGCATCTTGGAC
     ACTTGAGGTCGTACAAGACGACATTAAGACCGGAGGGACCGTAGAACCTG 7060       7070       7080       7090       7100
     TCCTGTTTCCTTTGCTCTGTCATCCCCGCGGTCAGCTCCTGCTGCGCAGC
     AGGACAAAGGAAACGAGACAGTAGGGGCGCCAGTCGAGGACGACGCGTCG 7110       7120       7130       7140       7150
     TTCTCAGCTGAAGTGCGTTTGGAGTGCCTGGCGTGTCTTGCTGGATCTTT
     AAGAGTCGACTTCACGCAAACCTCACGGACCGCACAGAACGACCTAGAAA 7160       7170       7180       7190       7200
     GAGTATTGCCTCTGGTTTCCTTGGTTCCTTCTGCTGAGTTGCTCAGCGTC
     CTCATAACGGAGACCAAAGGAACCAAGGAAGACGACTCAACGAGTCGCAG 7210       7220       7230       7240       7250
     TCCACTCCCCATTTCTTGTGTGGCCCTTCCTGCACTCCTCTGATTCCTTT
     AGGTGAGGGGTAAAGAACACACCGGGAAGGACGTGAGGAGACTAAGGAAA 7260       7270       7280       7290       7300
     TGTCTTCCCTGGTTTCTTGCTTTGGTTTCGAGTCTCCACAGAACTTTTGC
     ACAGAAGGGACCAAAGAACGAAACCAAAGCTCAGAGGTGTCTTGAAAACG 7310       7320       7330       7340       7350
     AGCTCTTCTGAAGACCTGGAAGCTTTTTCATCTTAATTCTCATCTCATGA
     TCGAGAAGACTTCTGGACCTTCGAAAAGTAGAATTAAGAGTAGAGTACT 7360       7370       7380       7390       7400
     CCTCTTTTCCCTTCTTTGAGAGCTAGAACTTCCCATGGTGAACTTCTCTT
     GGAGAAAAGGGAAGAAACTCTCGATCTTGAAGGGTACCACTTGAAGAGAA 7410       7420       7430       7440       7450
     TCCAGAATTCCATGCCTTCTTTTCCCTCCCACTTACCTGTTGTCCAGGAG
     AGGTCTTAAGGTACGGAAGAAAAGGGAGGGTGAATGGACAACAGGTCCTC 7460       7470       7480       7490       7500
     AGGTCAGATTGCTGTGCATATTGGAGGAGAACCCTTTCTTCCCTGGGCTC
     TCCAGTCTAACGACACGTATAACCTCCTCTTGGGAAAGAAGGGACCCGAG 7510       7520       7530       7540       7550
     TTCATCTCACATGACATCACCACATCACCTCGTTCCTTGGACCCTCAGTG
     AAGTAGAGTGTACTGTAGTGGTGTAGTGGAGCAAGGAACCTGGGAGTCAC
```

Figure 20

```
          7560      7570      7580      7590      7600
GTGTCACTGCTGGATTTTTCTTTCCTTTGGCTGGCCTTAGGGCACACCCA
CACAGTGACGACCTAAAAAGAAAGGAAACCGACCGGAATCCCGTGTGGGT 7610      7620      7630      7640      7650
GGTTGACTAGCGTAGTCATGGTATTTAGATCCACTCACATTTTCAGTTTC
CCAACTGATCGCATCAGTACCATAAATCTAGGTGAGTGTAAAAGTCAAAG 7660      7670      7680      7690      7700
TGTGTCTGTCTCTTGCCTGCTTCTGACTTCGCCCAGAGAAAGCTTCTCTT
ACACAGACAGAGAACGGACGAAGACTGAAGCGGGTCTCTTTCGAAGAGAA 7710      7720      7730      7740      7750
TCACAAGGGTTCTTAGATTTATGTTCACTGAGCACCTTCTTTTCTGAGGC
AGTGTTCCCAAGAATCTAAATACAAGTGACTCGTGGAAGAAAAGACTCCG 7760      7770      7780      7790      7800
AGTGTTTTACCAATATTTATTTTCCTAGTCAGTCTCGCCTTACCTTTCTT
TCACAAAATGGTTATAAATAAAAGGATCAGTCAGAGCGGAATGGAAAGAA 7810      7820      7830      7840      7850
GTTATGCATGTCTTTGGTCCTGACCCATTCTCTGAGTCTGTAAAATAGAA
CAATACGTACAGAAACCAGGACTGGGTAAGAGACTCAGACATTTTATCTT 7860      7870      7880      7890      7900
TTGCTGTATAATTTAATTACATGAAATCCTTTAGAATCTTAACACATCTT
AACGACATATTAAATTAATGTACTTTAGGAAATCTTAGAATTGTGTAGAA 7910      7920      7930      7940      7950
ACACCTGATTTAATATTTTATTGTATCCAAATTGAACCAACCCTATGTGA
TGTGGACTAAATTATAAATAACATAGGTTTAACTTGGTTGGGATACACT 7960      7970      7980      7990      8000
ATTTGACAGTGATTTCTCCCAGGGATCCTAGTGTATAAGGAATAGGACTT
TAAACTGTCACTAAAGAGGGTCCCTAGGATCACATATTCCTTATCCTGAA 8010      8020      8030      8040      8050
AGTATTTTCTATTTTTTGATATACCACATACCAGATACTGATTATGATGG
TCATAAAAGATAAAAACTATATGGTGTATGGTCTATGACTAATACTACC 8060      8070      8080      8090      8100
ACATTTAACCCTTTTTTCTCATTATGAAAGAAAGTTAGGAATTATTTCTT
TGTAAATTGGGAAAAAGAGTAATACTTTCTTTCAATCCTTAATAAAGAA
```

Figure 2P

```
        8110      8120      8130      8140      8150
CCAGTAGCGCCAGTGTAACCTGAAAGCCTTTGAAAGAGTAGTTTTTGTAT
GGTCATCGCGGTCACATTGGACTTTCGGAAACTTTCTCATCAAAAACATA 8160      8170      8180      8190      8200
AGCTATCTGAAAGGAATTTCTTTCCAAAATATTTTTCCAGTGCTGACAAC
TCGATAGACTTTCCTTAAAGAAAGGTTTTATAAAAAGGTCACGACTGTTG

>3'_GTVC_G0202
                                    |
        8210      8220      8230      8240      8250
AAACACGCAGACACACCCTGCAAGGTGAGTGTACGGCGCACTAGAGCATG
TTTGTGCGTCTGTGTGGGACGTTCCACTCACATGCCGCGTGATCTCGTAC

>AAV_ITR_(128bp)
                                    |
        8260      8270      8280      8290 |    8300
GCTACGTAGATAAGTAGCATGGCGGGTTAATCATTAACTACAAGGAACCC
CGATGCATCTATTCATCGTACCGCCCAATTAGTAATTGATGTTCCTTGGG 8310      8320      8330      8340      8350
CTAGTGATGGAGTTGGCCACTCCCTCTCTGCGCGCTCGCTCGCTCACTGA
GATCACTACCTCAACCGGTGAGGGAGAGACGCGCGAGCGAGCGAGTGACT 8360      8370      8380      8390      8400
GGCCGGGCGACCAAAGGTCGCCCGACGCCCGGGCTTTGCCCGGGCGGCCT
CCGGCCCGCTGGTTTCCAGCGGGCTGCGGGCCCGAAACGGGCCCGCCGGA 8410      8420      8430      8440      8450
CAGTGAGCGAGCGAGCGCGCAGCTGCCTGCAGGTCTGAGACAATAACCCT
GTCACTCGCTCGCTCGCGCGTCGACGGACGTCCAGACTCTGTTATTGGGA 8460      8470      8480      8490      8500
GATAAATGCTTCAATAATGTAAGCTTGTCGAGAAGTACTAGAGGATCATA
CTATTTACGAAGTTATTACATTCGAACAGCTCTTCATGATCTCCTAGTAT 8510      8520      8530      8540      8550
ATCAGCCATACCACATTTGTAGAGGTTTTACTTGCTTTAAAAAACCTCCC
TAGTCGGTATGGTGTAAACATCTCCAAAATGAACGAAATTTTTTGGAGGG 8560      8570      8580      8590      8600
ACACCTCCCCCTGAACCTGAAACATAAAATGAATGCAATTGTTGTTGTTA
TGTGGAGGGGGACTTGGACTTTGTATTTTACTTACGTTAACAACAACAAT
```

Figure 2Q

```
           8610       8620       8630       8640       8650
     ACTTGTTTATTGCAGCTTATAATGGTTACAAATAAAGCAATAGCATCACA
     TGAACAAATAACGTCGAATATTACCAATGTTTATTTCGTTATCGTAGTGT 8660       8670       8680       8690       8700
     AATTTCACAAATAAAGCATTTTTTTCACTGCATTCTAGTTGTGGTTTGTC
     TTAAAGTGTTTATTTCGTAAAAAAAGTGACGTAAGATCAACACCAAACAG 8710       8720       8730       8740       8750
     CAAACTCATCAATGTATCTTATCATGTCTGGATCTGATCACTGATATCGC
     GTTTGAGTAGTTACATAGAATAGTACAGACCTAGACTAGTGACTATAGCG

>Tb7L
                 |
           8760  |    8770       8780       8790       8800
     CTAGGAGATCCGAACCAGATAAGTGAAATCTAGTTCCAAACTATTTTGTC
     GATCCTCTAGGCTTGGTCTATTCACTTTAGATCAAGGTTTGATAAAACAG 8810       8820       8830       8840       8850
     ATTTTTAATTTTCGTATTAGCTTACGACGCTACACCCAGTTCCCATCTAT
     TAAAAATTAAAAGCATAATCGAATGCTGCGATGTGGGTCAAGGGTAGATA 8860       8870       8880       8890       8900
     TTTGTCACTCTTCCCTAAATAATCCTTAAAAACTCCATTTCCACCCCTCC
     AAACAGTGAGAAGGGATTTATTAGGAATTTTTGAGGTAAAGGTGGGGAGG 8910       8920       8930       8940       8950
     CAGTTCCCAACTATTTTGTCCGCCCACAGCGGGGCATTTTTCTTCCTGTT
     GTCAAGGGTTGATAAAACAGGCGGGTGTCGCCCCGTAAAAAGAAGGACAA 8960       8970       8980       8990       9000
     ATGTTTTTAATCAAACATCCTGCCAACTCCATGTGACAAACCGTCATCTT
     TACAAAAATTAGTTTGTAGGACGGTTGAGGTACACTGTTTGGCAGTAGAA 9010       9020       9030       9040       9050
     CGGCTACTTTTTCTCTGTCACAGAATGAAAATTTTTCTGTCATCTCTTCG
     GCCGATGAAAAGAGACAGTGTCTTACTTTTAAAAGACAGTAGAGAAGC 9060       9070       9080       9090       9100
     TTATTAATGTTTGTAATTGACTGAATATCAACGCTTATTTGCAGCCTGAA
     AATAATTACAAACATTAACTGACTTATAGTTGCGAATAAACGTCGGACTT
```

Figure 2R

```
      9110
TGGCGAATGG
ACCGCTTACC
```

Figure 3A stuffer sequence
GAATTCGGGCTATCCCAGGTTGCCTTGGTTCATGGCAAATGGGACGTTAAGAGGGCA
GAGAGAATATGAACAGAAACTGTTCTAATATTGGTCATTTAATGTGTAAGTATTGTT
CTTTTTTAAACCTCCTTCATTTTTTTTCCAGGAATTGCTGGACACAGTGGCTTGGTGT
GTGTCTGAGGACTGTAGGCCATGGCCCTAGGTTGTGGTTTTAGGTCTCAGGTGCTCT
TCCTGGCTGTCTCCTTGCTTCTTTCCCATGTCCTCTTCTTTGTTTCCAGCCATTTCTCC
CTTATGCTTAAGTTTGGTGCAGCAGGGTTTGGCTGCTCTCAGATTCCTGCTTCCTCAG
ATGCTGTAGTTGTCAGGCCCAGCGGGCTGGCAGCGGGATCAGGATCTGGCTAGGTTT
GCTCTCACTGTGGCAGAGTAGGGGGAGGCGTGGGAGAGCACGTGTGACCCCAGGCCA
GCTGTAGGGAGCATAGGCATGGTCACGTAGCCTTCAGGTCCTAGACTTTGTCTTCTCA
TGAGTATGGCTGTGTGTGTATGGTGAAAACTAGGTTCTACTTAGCCCAAGAAAATGG
GCACATTTTGCATGTGGTTTCTGTAGAGAAATGCACTGGGTATCTGACATAGCCTGG
CAGCATGCCTCCCTCAGGTAGGTTAGTCTCAGGCGGTGAAGCACGTGTGTCCAGCAAG
AACTTCATATGTGGCATAAAGTCTCCGTTCTGTGAGGTGCTGGCAAATCACCACCACC
GTCAAGAGGCTGAAGTGATTTTTGTCTAGGGAGGCAGGAAAGGCTTCCTGGAGTCAG
CAGCCAGTAGGTGAAAGAGTAGATTGGAGACCTTCTTAATCATCACCGCCTCTTGTC
TCAAGGGGTGCCAGGAAGCTGTGGAGGCTGAACCCATCTTATGCTGCCAGAGAGTGG
GACACCATGAGGGTCAGGTCAAGGGGTTGTACCTTGTTTGGTAGAGAATTAGGGGCT
CTTGAAGACTTTGGATGTGGTCAGGGGAGTGTATCATTTAGGAAGAGTGACCCGGTG
AGGACGTGGGGTAGAGGAGGACAGGTGGGAGGGAGTCCAGGTGGGAGTGAGTAGACC
CAGCAGGAGTGCAGGGCCTCGAGCCAGGATGGTGGCAGGGCTGTGAGGAGAGGCAGC
CACCTGTGTGTCTGCGGAAGCAGGGGCAAGAGGGAAGAGGCCAGCAGCGTGCTGCCA
TCACCCAGCGACTGGCGTAGATTGTGAGAGACCATTCCCTGCTCTTAGGAGGGGCTG
AGTTTTAGTTTTCTCTTGTTATACAATAAGCTTGGTATTTGTTTACAAAACATTTGT
AAAGCTAAATCAAGGTTTGATAAGGCTTCTAGTTTTATTTAAGAAGTAATGTTGAAA
TAAATGTTTGTCCAATTCGCTTTGCTCATTTAAGGACTTTCAGTACAAACTGCAACA
ACAGGATTAGGATTTAAACGTTTCTGAGATGTTTTTACTCCTCAGAATTTCCCAGAA
TGTGATCTGGTTTTGATTTTCAAGCTTGCTGACCCAATAGGTTAACCCACAAGTTTT
ACGAAGACCATCTCAGTCCACTTACATCAACTGCCCATGCCACGGTTAAAGAGATCAT
CGACTGATGTTTGGCACAGCTTCCTCCCTCTTGGGTGGGCAAGCATTTGGAAGAGAA
GGCTCCTATGGGTGAGAGTGGGGCACCAAAGTCTTCCCTGTCCCATCCCCTAGCTTGA
GAAGCCCTTCTCTAATGTGGACTTTGTGCCGTTAGCATCGTTACTAGCTTGAAGTTG
ACCATCTGGACGTACTTTCTGGTTTAGCCTCACAAGTGAGCAAGGAGGGTTGAGAGA
TGTGCTGTGAGGAATGTGGGGCCCCAGCTGGCAGCAGGCTCTGGGTCAGGGGGCAG
GGACCACGGGCATACCTGACAGTGAGGAGGGTCTAGTAGGGGATCAGTTCCCCTGTT
GTTCTTTAGAATTTTCTGGATATTCTTCTTTATTGATTTTGGGATGTGAACAATAGA
ATCAACTTCTACTTGTAGATTGATTTAGGGAGAACTTATACCTCAGATGTTAAGTCA
CCCTGTCCAGAATGTGGGATGCTTTCCTATTTGTTCAGAACTTTTTAAATTACCTCAG
AAGCACATGAAATTTAAAGGATTTTAAAAAAACTTAAAGATTATTTCACATAGCTC
TTGCACATTTCTTGATAAATGAATCCTCAGGTATTCCTCTGTTTTGTTACTAATAG
TTACTTCTTATGGGTTTTTTTTCCCCTGAAAATCATTTATCAAACGTATGTGGCTTA
TTTTCTGAAGGATGTTTGATAATTTTGGAAGATATGAAAGTCTTCATATTTTACAAG
GTTTGAGGTCTCTTTAAGCTGCATGGTTCTCATGTCAGCTCCCAAAGCAGAAGACGG
CATGTTGAAAAATGCCGTAGAGAAGATACTTCTTTTCCACCTGTTTTCAACTCATAT
CATCTTGAATTTCAGGGCACCTTTCCATGCTCCTAGTGCTTGCTATCTGTTTATTATT
TTCCTTCCTGAATACCCTGAACTCCAGCATGTTCTGCTGTAATTCT

Figure 3B

GGCCTCCCTGGCATCTTGGACTCCTGTTTCCTTTGCTCTGTCATCCCCGCGGTCAGCT
CCTGCTGCGCAGCTTCTCAGCTGAAGTGCGTTTGGAGTGCCTGGCGTGTCTTGCTGGA
TCTTTGAGTATTGCCTCTGGTTTCCTTGGTTCCTTCTGCTGAGTTGCTCAGCGTCTCC
ACTCCCCATTTCTTGTGTGGCCCTTCCTGCACTCCTCTGATTCCTTTTGTCTTCCCTGG
TTTCTTGCTTTGGTTTCGAGTCTCCACAGAACTTTTGCAGCTCTTCTGAAGACCTGGA
AGCTTTTTCATCTTAATTCTCATCTCATGACCTCTTTTCCCTTCTTTGAGAGCTAGAA
CTTCCCATGGTGAACTTCTCTTTCCAGAATTCCATGCCTTCTTTTCCCTCCCACTTAC
CTGTTGTCCAGGAGAGGTCAGATTGCTGTGCATATTGGAGGAGAACCCTTTCTTCCCT
GGGCTCTTCATCTCACATGACATCACCACATCACCTCGTTCCTTGGACCCTCAGTGGT
GTCACTGCTGGATTTTCTTTCCTTTGGCTGGCCTTAGGGCACACCCAGGTTGACTAG
CGTAGTCATGGTATTTAGATCCACTCACATTTTCAGTTTCTGTGTCTGTCTCTTGCCT
GCTTCTGACTTCGCCCAGAGAAAGCTTCTCTTTCACAAGGGTTCTTAGATTTATGTTC
ACTGAGCACCTTCTTTTCTGAGGCAGTGTTTTACCAATATTTATTTTCCTAGTCAGTC
TCGCCTTACCTTTCTTGTTATGCATGTCTTTGGTCCTGACCCATTCTCTGAGTCTGTA
AAATAGAATTGCTGTATAATTTAATTACATGAAATCCTTTAGAATCTTAACACATCT
TACACCTGATTTAATATTTTATTGTATCCAAATTGAACCAACCCTATGTGAATTTGA
CAGTGATTTCTCCCAGGGATCCTAGTGTATAAGGAATAGGACTTAGTATTTTCTATT
TTTTGATATACCACATACCAGATACTGATTATGATGGACATTTAACCCTTTTTTCTC
ATTATGAAAGAAAGTTAGGAATTATTTCTTCCAGTAGCGCCAGTGTAACCTGAAAGC
CTTTGAAAGAGTAGTTTTTGTATAGCTATCTGAAAGGAATTTCTTTCCAAAATATTT
TTCCAGTGCTGACAACAAACACGCAGACACACCCTGCAAGGTGAGTGTACGGCG mHDS1 sequence
CTCGAGTGAGCGATGCTGGCTCGCATGGTCGATACTGTAAAGCCACAGATGGGTGTC
GACCATGCGAGCCAGCACCGCCTACTAGA mU6 promoter
CGACGCCGCCATCTCTAGGCCCGCGCCGGCCCCCTCGCACAGACTTGTGGGAGAAGCT
CGGCTACTCCCCTGCCCCGGTTAATTTGCATATAATATTTCCTAGTAACTATAGAGGC
TTAATGTGCGATAAAAGACAGATAATCTGTTCTTTTAATACTAGCTACATTTTACA
TGATAGGCTTGGATTTCTATAAGAGATACAAATACTAAATTATTATTTTAAAAAACA
GCACAAAAGGAAACTCACCCTAACTGTAAAGTAATTGTGTGTTTTGAGACTATAAAT
ATCCCTTGGAGAAAAGCCTTGTTT AAV2 ITR (94bp)
CTGCGCGCTCGCTCGCTCACTGAGGCCGCCCGGGCGTCGGGCGACCTTTGGTCGCCCG
GCCTCAGTGAGCGAGCGAGCGCGCAGAGAGGGAGTG AAV2 ITR (128bp)
AAGGAACCCCTAGTGATGGAGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTGAG
CGAGCGAGCGCG

Figure 3C

Gentamicin
TTAGGTGGCGGTACTTGGGTCGATATCAAAGTGCATCACTTCTTCCCGTATGCCCAAC
TTTGTATAGAGAGCCACTGCGGGATCGTCACCGTAATCTGCTTGCACGTAGATCACA
TAAGCACCAAGCGCGTTGGCCTCATGCTTGAGGAGATTGATGAGCGCGGTGGCAATG
CCCTGCCTCCGGTGCTCGCCGGAGACTGCGAGATCATAGATATAGATCTCACTACGCG
GCTGCTCAAACTTGGGCAGAACGTAAGCCGCGAGAGCGCCAACAACCGCTTCTTGGTC
GAAGGCAGCAAGCGCGATGAATGTCTTACTACGGAGCAAGTTCCCGAGGTAATCGGA
GTCCGGCTGATGTTGGGAGTAGGTGGCTACGTCTCCGAACTCACGACCGAAAAGATC
AAGAGCAGCCCGCATGGATTTGACTTGGTCAGGGCCGAGCCTACATGTGCGAATGAT
GCCCATACTTGAGCCACCTAACTTTGTTTTAGGGCGACTGCCCTGCTGCGTAACATCG
TTGCTGCTGCGTAACAT Beta-lactamase (Ampicillin)
ATGAGTATTCAACATTTCCGTGTCGCCCTTATTCCCTTTTTTGCGGCATTTTGCCTTC
CTGTTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGC
GGTATTATCCCGTATTGACGCCGGGCAAGAGCAACTCGGTCGCCGCATACACTATTCT
CAGAATGACTTGGTTGAGTACTCACCAGTCACAGAAAAGCATCTTACGGATGGCATG
ACAGTAAGAGAATTATGCAGTGCTGCCATAACCATGAGTGATAACACTGCGGCCAAC
TTACTTCTGACAACGATCGGAGGACCGAAGGAGCTAACCGCTTTTTTGCACAACATG
GGGGATCATGTAACTCGCCTTGATCGTTGGGAACCGGAGCTGAATGAAGCCATACCA
AACGACGAGCGTGACACCACGATGCCTGTAGCAATGGCAACAACGTTGCGCAAACTA
TTAACTGGCGAACTACTTACTCTAGCTTCCCGGCAACAATTAATAGACTGGATGGAG
GCGGATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGGGC
CAGATGGTAAGCCCTCCCGTATCGTAGTTATCTACACGACGGGGAGTCAGGCAACTA
TGGATGAACGAAATAGACAGATCGCTGAGATAGGTGCCTCACTGATTAAGCATTGGT
AA Tn7R (Transposable element)
TGTGGGCGGACAATAAAGTCTTAAACTGAACAAAATAGATCTAAACTATGACAATAA
AGTCTTAAACTAGACAGAATAGTTGTAAACTGAAATCAGTCCAGTTATGCTGTGAAA
AAGCATACTGGACTTTTGTTATGGCTAAAGCAAACTCTTCATTTTCTGAAGTGCAAA
TTGCCCGTCGTATTAAAGAGGGGCGTGGCCAAGGGCATGGTAAAGACTATATTC Tb7L (Transposable element)
AACCAGATAAGTGAAATCTAGTTCCAAACTATTTTGTCATTTTTAATTTTCGTATTA
GCTTACGACGCTACACCCAGTTCCCATCTATTTTGTCACTCTTCCCTAAATAATCCTT
AAAAACTCCATTTCCACCCCTCCCAGTTCCCAACTATTTTGTCCGCCCACA

5pFBAAVmU6miHDS1-stuffer

Map Features:

| 494 – 1354 | Beta-lactamase |
| --- | --- |
| 2418 – 2642 | Tn7R |
| 27009 – 3242 | Gentamicin |
| 3810 – 3928 | AAV ITR (119bp) |
| 3967 – 4249 | mU6 promoter |
| 4332 – 4417 | miHDS1 |
| 4465 – 8239 | Stuffer sequence |
| 8293 – 8423 | AAV ITR (130bp) |
| 8764 – 8929 | Tb7L |

Figure 6A

Plasmid sequence (SEQ ID NO:12):

```
TTCGCTTTCTTCCCTTCCTTTCTCGCCACGTTCGCCGGCTTTCCCCGTCAAGCTCTAAA
TCGGGGGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTTTCGCC
CTTTGACGTTGGAGTCCACGTTCTTAATAGTGGACTCTTGTTCCAAACTGGAACAAC
ACTCAACCCTATCTCGGTCTATTCTTTTGATTTATAAGGGATTTTGCCGATTTCGGCC
TATTGGTTAAAAAATGAGCTGATTTAACAAAATTTAACGCGAATTTTAACAAAATA
TTAACGCTTACAATTTAGGTGGCACTTTTCGGGGAAATGTGCGCGGAACCCCTATTT
GTTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCT
GGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAAT
GATGAGCACTTTTAAAGTTCTGCTATGTGGCGCGGTATTATCCCGTATTGACGCCGG
GCAAGAGCAACTCGGTCGCCGCATACACTATTCTCAGAATGACTTGGTTGAGTACTC
ACCAGTCACAGAAAAGCATCTTACGGATGGCATGACAGTAAGAGAATTATGCAGTGC
TGCCATAACCATGAGTGATAACACTGCGGCCAACTTACTTCTGACAACGATCGGAGG
ACCGAAGGAGCTAACCGCTTTTTTGCACAACATGGGGGATCATGTAACTCGCCTTGA
TCGTTGGGAACCGGAGCTGAATGAAGCCATACCAAACGACGAGCGTGACACCACGAT
GCCTGTAGCAATGGCAACAACGTTGCGCAAACTATTAACTGGCGAACTACTTACTCT
AGCTTCCCGGCAACAATTAATAGACTGGATGGAGGCGGATAAAGTTGCAGGACCACT
TCTGCGCTCGGCCCTTCCGGCTGGCTGGTTTATTGCTGATAAATCTGGAGCCGGTGAG
CGTGGGTCTCGCGGTATCATTGCAGCACTGGGGCCAGATGGTAAGCCCTCCCGTATCG
TAGTTATCTACACGACGGGGAGTCAGGCAACTATGGATGAACGAAATAGACAGATCG
CTGAGATAGGTGCCTCACTGATTAAGCATTGGTAACTGTCAGACCAAGTTTACTCAT
ATATACTTTAGATTGATTTAAAACTTCATTTTTAATTTAAAAGGATCTAGGTGAAGA
TCCTTTTTGATAATCTCATGACCAAAATCCCTTAACGTGAGTTTTCGTTCCACTGAGC
GTCAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGCAGATACC
AAATACTGTTCTTCTAGTGTAGCCGTAGTTAGGCCACCACTTCAAGAACTCTGTAGC
ACCGCCTACATACCTCGCTCTGCTAATCCTGTTACCAGTGGCTGCTGCCAGTGGCGAT
AAGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACACCG
AACTGAGATACCTACAGCGTGAGCTATGAGAAAGCGCCACGCTTCCCGAAGGGAGAA
AGGCGGACAGGTATCCGGTAAGCGGCAGGGTCGGAACAGGAGAGCGCACGAGGGAGC
TTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAG
CAACGCGGCCTTTTTACGGTTCCTGGCCTTTTGCTGGCCTTTTGCTCACATGTTCTTT
CCTGCGTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAGCGGAAG
AGCGCCTGATGCGGTATTTTCTCCTTACGCATCTGTGCGGTATTTCACACCGCATAGA
CCAGCCGCGTAACCTGGCAAAATCGGTTACGGTTGAGTAATAAATGGATGCCCTGCG
TAAGCGGGTGTGGGCGGACAATAAAGTCTTAAACTGAACAAAATAGATCTAAACTAT
GACAATAAAGTCTTAAACTAGACAGAATAGTTGTAAACTGAAAT
```

Figure 6B

```
CAGTCCAGTTATGCTGTGAAAAAGCATACTGGACTTTTGTTATGGCTAAAGCAAACT
CTTCATTTTCTGAAGTGCAAATTGCCCGTCGTATTAAAGAGGGGCGTGGCCAAGGGC
ATGGTAAAGACTATATTCGCGGCGTTGTGACAATTTACCGAACAACTCCGCGGCCGG
GAAGCCGATCTCGGCTTGAACGAATTGTTAGGTGGCGGTACTTGGGTCGATATCAAA
GTGCATCACTTCTTCCCGTATGCCCAACTTTGTATAGAGAGCCACTGCGGGATCGTCA
CCGTAATCTGCTTGCACGTAGATCACATAAGCACCAAGCGCGTTGGCCTCATGCTTGA
GGAGATTGATGAGCGCGGTGGCAATGCCCTGCCTCCGGTGCTCGCCGGAGACTGCGAG
ATCATAGATATAGATCTCACTACGCGGCTGCTCAAACTTGGGCAGAACGTAAGCCGC
GAGAGCGCCAACAACCGCTTCTTGGTCGAAGGCAGCAAGCGCGATGAATGTCTTACT
ACGGAGCAAGTTCCCGAGGTAATCGGAGTCCGGCTGATGTTGGGAGTAGGTGGCTAC
GTCTCCGAACTCACGACCGAAAAGATCAAGAGCAGCCCGCATGGATTTGACTTGGTC
AGGGCCGAGCCTACATGTGCGAATGATGCCCATACTTGAGCCACCTAACTTTGTTTTA
GGGCGACTGCCCTGCTGCGTAACATCGTTGCTGCTGCGTAACATCGTTGCTGCTCCAT
AACATCAAACATCGACCCACGGCGTAACGCGCTTGCTGCTTGGATGCCCGAGGCATAG
ACTGTACAAAAAAACAGTCATAACAAGCCATGAAAACCGCCACTGCGCCGTTACCAC
CGCTGCGTTCGGTCAAGGTTCTGGACCAGTTGCGTGAGCGCATACGCTACTTGCATTA
CAGTTTACGAACCGAACAGGCTTATGTCAACTGGGTTCGTGCCTTCATCCGTTTCCAC
GGTGTGCGTCACCCGGCAACCTTGGGCAGCAGCGAAGTCGAGGCATTTCTGTCCTGGC
TGGCGAACGAGCGCAAGGTTTCGGTCTCCACGCATCGTCAGGCATTGGCGGCCTTGCT
GTTCTTCTACGGCAAGGTGCTGTGCACGGATCTGCCCTGGCTTCAGGAGATCGGAAG
ACCTCGGCCGTCGCGGCGCTTGCCGGTGGTGCTGACCCCGGATGAAGTGGTTCGCATC
CTCGGTTTTCTGGAAGGCGAGCATCGTTTGTTCGCCCAGGACTCTAGCTATAGTTCTA
GTGGTTGGCTACAGCTTGCATGCCTGCAGGCAGCTGCGCGCTCGCTCGCTCACTGAGG
CCGCCCGGGCGTCGGGCGACCTTTGGTCGCCCGGCCTCAGTGAGCGAGCGAGCGCGCA
GAGAGGGAGTGGCCAACTCCATCACTAGGGGTTCCTTGTAGTTAATGATTAACCCGC
CATGCTACTTATCTACGTAGCCATGCTCTAGTGAATTCGACGCCGCCATCTCTAGGCC
CGCGCCGGCCCCCTCGCACAGACTTGTGGGAGAAGCTCGGCTACTCCCCTGCCCCGGT
TAATTTGCATATAATATTTCCTAGTAACTATAGAGGCTTAATGTGCGATAAAAGACA
GATAATCTGTTCTTTTTAATACTAGCTACATTTTACATGATAGGCTTGGATTTCTAT
AAGAGATACAAATACTAAATTATTATTTTAAAAAACAGCACAAAAGGAAACTCACCC
TAACTGTAAAGTAATTGTGTGTTTTGAGACTATAAATATCCCTTGGAGAAAAGCCTT
GTTTGCGTTTAGTGAACCGTCAGATGGTACCGTTTAAACTCGAGTGAGCGATGCTGG
CTCGCATGGTCGATACTGTAAAGCCACAGATGGGTGTCGACCATGCGAGCCAGCACCG
CCTACTAGAGCGGCCGCCACAGCGGGGAGATCCAGACATGATAAGATACATTTTTG
AATTCGGGCTATCCCAGGTTGCCTTGGTTCATGGCAAATGGGACGTTAAGAGGGCAG
AGAGAATATGAACAGAAACTGTTCTAATATTGGTCATTTAATGTGTAAGTATTGTTC
TTTTTTAAACCTCCTTCATTTTTTTTCCAGGAATTGCTGGACACAGTGGCTTGGTGTG
TGTCTGAGGACTGTAGGCCATGGCCCTAGGTTGTGGTTTTAGGTCTCAGGTGCTCTTC
CTGGCTGTCTCCTTGCTTCTTTCCCATGTCCTCTTCTTTGTTTCCAGCCATTTCTCCCT
TATGCTTAAGTTTGGTGCAGCAGGGTTTGGCTGCTCTCAGATTCCTGCTTCCTCAGAT
GCTGTAGTTGTCAGGCCCAGCGGGCTGGCAGCGGGATCAGGATCTGGCTAGGTTTGC
TCTCACTGTGGCAGAGTAGGGGGAGGCGTGGGAGAGCACGTGTGACCCCAGGCCAGC
TGTAGGGAGCATAGGCATGGTCACGTAGCCTTCAGGTCCTAGACTTTGTCTTCTCATG
AGTATGGCTGTGTGTGTATGGTGAAAACTAGGTTCTACTTAGCCCAAGAAAATGGGC
ACATTTTGCATGTGGTTTCTGTAGAGAAATGCACTGGGTATCTGACATAGCCTGGCA
GCATGCCTCCCTCAGGTAGGTTAGTCTCAGGCGGTGAAGCACG
```

Figure 6C

TGTGTCCAGCAAGAACTTCATATGTGGCATAAAGTCTCCGTTCTGTGAGGTGCTGGC
AAATCACCACCACCGTCAAGAGGCTGAAGTGATTTTTGTCTAGGGAGGCAGGAAAGG
CTTCCTGGAGTCAGCAGCCAGTAGGTGAAAGAGTAGATTGGAGACCTTCTTAATCAT
CACCGCCTCTTGTCTCAAGGGGTGCCAGGAAGCTGTGGAGGCTGAACCCATCTTATGC
TGCCAGAGAGTGGGACACCATGAGGGTCAGGTCAAGGGGTTGTACCTTGTTTGGTAG
AGAATTAGGGGCTCTTGAAGACTTTGGATGTGGTCAGGGGAGTGTATCATTTAGGAA
GAGTGACCCGGTGAGGACGTGGGGTAGAGGAGGACAGGTGGGAGGGAGTCCAGGTGG
GAGTGAGTAGACCCAGCAGGAGTGCAGGGCCTCGAGCCAGGATGGTGGCAGGGCTGT
GAGGAGAGGCAGCCACCTGTGTGTCTGCGGAAGCAGGGGCAAGAGGGAAGAGGCCAG
CAGCGTGCTGCCATCACCCAGCGACTGGCGTAGATTGTGAGAGACCATTCCCTGCTCT
TAGGAGGGGCTGAGTTTTAGTTTTCTCTTGTTATACAATAAGCTTGGTATTTGTTTA
CAAAACATTTGTAAAGCTAAATCAAGGTTTGATAAGGCTTCTAGTTTTATTTAAGAA
GTAATGTTGAAATAAATGTTTGTCCAATTCGCTTTGCTCATTTAAGGACTTTCAGTA
CAAACTGCAACAACAGGATTAGGATTTAAACGTTTCTGAGATGTTTTTACTCCTCAG
AATTTCCCAGAATGTGATCTGGTTTTGATTTTCAAGCTTGCTGACCCAATAGGTTAA
CCCACAAGTTTTACGAAGACCATCTCAGTCCACTTACATCAACTGCCCATGCCACGGT
TAAAGAGATCATCGACTGATGTTTGGCACAGCTTCCTCCCTCTTGGGTGGGCAAGCA
TTTGGAAGAGAAGGCTCCTATGGGTGAGAGTGGGGCACCAAAGTCTTCCCTGTCCCA
TCCCCTAGCTTGAGAAGCCCTTCTCTAATGTGGACTTTGTGCCGTTAGCATCGTTACT
AGCTTGAAGTTGACCATCTGGACGTACTTTCTGGTTTAGCCTCACAAGTGAGCAAGG
AGGGTTGAGAGATGTGCTGTGAGGAATGTGGGGCCCCAGCTGGCAGCAGGCTCTGGG
TCAGGGGGGCAGGGACCACGGGCATACCTGACAGTGAGGAGGGGTCTAGTAGGGGAT
CAGTTCCCCTGTTGTTCTTTAGAATTTTCTGGATATTCTTCTTTATTGATTTGGGAT
GTGAACAATAGAATCAACTTCTACTTGTAGATTGATTTAGGGAGAACTTATACCTCA
GATGTTAAGTCACCCTGTCCAGAATGTGGGATGCTTTCCTATTTGTTCAGAACTTTT
TAAATTACCTCAGAAGCACATGAAATTTAAAGGATTTTAAAAAAAACTTAAAGATTA
TTTCACATAGCTCTTGCACATTTCTTGATAAATGAATCCTCAGGTATTCCTCTGTTTT
TGTTACTAATAGTTACTTCTTATGGGTTTTTTTTCCCTGAAAATCATTTATCAAAC
GTATGTGGCTTATTTTCTGAAGGATGTTTGATAATTTTGGAAGATATGAAAGTCTTC
ATATTTTACAAGGTTTGGGGTCTCTTTAAGCTGCATGGTTCTCATGTCAGCTCCCAA
AGCAGAAGACGGCATGTTGAAAAATGCCGTAGAGAAGATACTTCTTTTCCACCTGTT
TTCAACTCATATCATCTTGAATTTCAGGGCACCTTTCCATGCTCCTAGTGCTTGCTAT
CTGTTTATTATTTTCCTTCCTGAATACCCTGAACTCCAGCATGTTCTGCTGTAATTCT
GGCCTCCCTGGCATCTTGGACTCCTGTTTCCTTTGCTCTGTCATCCCCGCGGTCAGCT
CCTGCTGCGCAGCTTCTCAGCTGAAGTGCGTTTGGAGTGCCTGGCGTGTCTTGCTGGA
TCTTTGAGTATTGCCTCTGGTTTCCTTGGTTCCTTCTGCTGAGTTGCTCAGCGTCTCC
ACTCCCCATTTCTTGTGTGGCCCTTCCTGCACTCCTCTGATTCCTTTTGTCTTCCCTGG
TTTCTTGCTTTGGTTTCGAGTCTCCACAGAACTTTTGCAGCTCTTCTGAAGACCTGGA
AGCTTTTTCATCTTAATTCTCATCTCATGACCTCTTTTCCCTTCTTTGAGAGCTAGAA
CTTCCCATGGTGAACTTCTCTTTCCAGAATTCCATGCCTTCTTTTCCCTCCCACTTAC
CTGTTGTCCAGGAGAGGTCAGATTGCTGTGCATATTGGAGGAGAACCCTTTCTTCCCT
GGGCTCTTCATCTCACATGACATCACCACATCACCTCGTTCCTTGGACCCTCAGTGGT
GTCACTGCTGGATTTTTCTTTCCTTTGGCTGGCCTTAGGGCACACCCAGGTTGACTAG
CGTAGTCATGGTATTTAGATCCACTCACATTTTCAGTTTCTGTGTCTGTCTCTTGCCT
GCTTCTGACTTCGCCCAGAGAAAGCTTCTCTTTCACAAGGGTTCTTAGATTTATGTTC
ACTGAGCACCTTCTTTTCTGAGGCAGTGTTTTACCAATATTTATT

Figure 6D

```
TTCCTAGTCAGTCTCGCCTTACCTTTCTTGTTATGCATGTCTTTGGTCCTGACCCATT
CTCTGAGTCTGTAAAATAGAATTGCTGTATAATTTAATTACATGAAATCCTTTAGAA
TCTTAACACATCTTACACCTGATTTAATATTTTATTGTATCCAAATTGAACCAACCCT
ATGTGAATTTGACAGTGATTTCTCCCAGGGATCCTAGTGTATAAGGAATAGGACTTA
GTATTTTCTATTTTTTGATATACCACATACCAGATACTGATTATGATGGACATTTAA
CCCTTTTTTCTCATTATGAAAGAAAGTTAGGAATTATTTCTTCCAGTAGCGCCAGTG
TAACCTGAAAGCCTTTGAAAGAGTAGTTTTTGTATAGCTATCTGAAAGGAATTTCTT
TCCAAAATATTTTTCCAGTGCTGACAACAAACACGCAGACACACCCTGCAAGGTGAG
TGTACGGCGCACTAGAGCATGGCTACGTAGATAAGTAGCATGGCGGGTTAATCATTA
ACTACAAGGAACCCCTAGTGATGGAGTTGGCCACTCCCTCTCTGCGCGCTCGCTCGCT
CACTGAGGCCGGGCGACCAAAGGTCGCCCGACGCCCGGGCTTTGCCCGGGCGGCCTCA
GTGAGCGAGCGAGCGCGCAGCTGCCTGCAGGTCTGAGACAATAACCCTGATAAATGC
TTCAATAATGTAAGCTTGTCGAGAAGTACTAGAGGATCATAATCAGCCATACCACAT
TTGTAGAGGTTTTACTTGCTTTAAAAAACCTCCCACACCTCCCCCTGAACCTGAAACA
TAAAATGAATGCAATTGTTGTTGTTAACTTGTTTATTGCAGCTTATAATGGTTACAA
ATAAAGCAATAGCATCACAAATTTCACAAATAAAGCATTTTTTTCACTGCATTCTAG
TTGTGGTTTGTCCAAACTCATCAATGTATCTTATCATGTCTGGATCTGATCACTGAT
ATCGCCTAGGAGATCCGAACCAGATAAGTGAAATCTAGTTCCAAACTATTTTGTCAT
TTTTAATTTTCGTATTAGCTTACGACGCTACACCCAGTTCCCATCTATTTTGTCACTC
TTCCCTAAATAATCCTTAAAAACTCCATTTCCACCCCTCCCAGTTCCCAACTATTTTG
TCCGCCCACAGCGGGGCATTTTTCTTCCTGTTATGTTTTAATCAAACATCCTGCCAA
CTCCATGTGACAAACCGTCATCTTCGGCTACTTTTTCTCTGTCACAGAATGAAAATTT
TTCTGTCATCTCTTCGTTATTAATGTTTGTAATTGACTGAATATCAACGCTTATTTG
CAGCCTGAATGGCGAATGG
```

Figure 7A

Stuffer sequence (Stuffer #2) (SEQ ID NO:2)

GGGCTATCCCAGGTTGCCTTGGTTCATGGCAAATGGGACGTTAAGAGGGCAGAGAGA
ATATGAACAGAAACTGTTCTAATATTGGTCATTTAATGTGTAAGTATTGTTCTTTTT
TAAACCTCCTTCATTTTTTTCCAGGAATTGCTGGACACAGTGGCTTGGTGTGTGTCT
GAGGACTGTAGGCCATGGCCCTAGGTTGTGGTTTTAGGTCTCAGGTGCTCTTCCTGGC
TGTCTCCTTGCTTCTTTCCCATGTCCTCTTCTTTGTTTCCAGCCATTTCTCCCTTATGC
TTAAGTTTGGTGCAGCAGGGTTTGGCTGCTCTCAGATTCCTGCTTCCTCAGATGCTGT
AGTTGTCAGGCCCAGCGGGCTGGCAGCGGGATCAGGATCTGGCTAGGTTTGCTCTCAC
TGTGGCAGAGTAGGGGGAGGCGTGGGAGAGCACGTGTGACCCCAGGCCAGCTGTAGG
GAGCATAGGCATGGTCACGTAGCCTTCAGGTCCTAGACTTTGTCTTCTCATGAGTAT
GGCTGTGTGTATGGTGAAAACTAGGTTCTACTTAGCCCAAGAAAATGGGCACATT
TTGCATGTGGTTTCTGTAGAGAAATGCACTGGGTATCTGACATAGCCTGGCAGCATG
CCTCCCTCAGGTAGGTTAGTCTCAGGCGGTGAAGCACGTGTGTCCAGCAAGAACTTCA
TATGTGGCATAAAGTCTCCGTTCTGTGAGGTGCTGGCAAATCACCACCACCGTCAAG
AGGCTGAAGTGATTTTTGTCTAGGGAGGCAGGAAAGGCTTCCTGGAGTCAGCAGCCA
GTAGGTGAAAGAGTAGATTGGAGACCTTCTTAATCATCACCGCCTCTTGTCTCAAGG
GGTGCCAGGAAGCTGTGGAGGCTGAACCCATCTTATGCTGCCAGAGAGTGGGACACC
ATGAGGGTCAGGTCAAGGGGTTGTACCTTGTTTGGTAGAGAATTAGGGGCTCTTGAA
GACTTTGGATGTGGTCAGGGGAGTGTATCATTTAGGAAGAGTGACCCGGTGAGGACG
TGGGGTAGAGGAGGACAGGTGGGAGGGAGTCCAGGTGGGAGTGAGTAGACCCAGCAG
GAGTGCAGGGCCTCGAGCCAGGATGGTGGCAGGGCTGTGAGGAGAGGCAGCCACCTG
TGTGTCTGCGGAAGCAGGGGCAAGAGGGAAGAGGCCAGCAGCGTGCTGCCATCACCC
AGCGACTGGCGTAGATTGTGAGAGACCATTCCCTGCTCTTAGGAGGGGCTGAGTTTT
AGTTTTCTCTTGTTATACAATAAGCTTGGTATTTGTTTACAAAACATTTGTAAAGCT
AAATCAAGGTTTGATAAGGCTTCTAGTTTTATTTAAGAAGTAATGTTGAAATAAATG
TTTGTCCAATTCGCTTTGCTCATTTAAGGACTTTCAGTACAAACTGCAACAACAGGA
TTAGGATTTAAACGTTTCTGAGATGTTTTACTCCTCAGAATTTCCCAGAATGTGAT
CTGGTTTTGATTTTCAAGCTTGCTGACCCAATAGGTTAACCCACAAGTTTTACGAAG
ACCATCTCAGTCCACTTACATCAACTGCCCATGCCACGGTTAAAGAGATCATCGACTG
ATGTTTGGCACAGCTTCCTCCCTCTTGGGTGGGCAAGCATTTGGAAGAGAAGGCTCCT
ATGGGTGAGAGTGGGGCACCAAAGTCTTCCCTGTCCATCCCCTAGCTTGAGAAGCCC
TTCTCTAATGTGGACTTTGTGCCGTTAGCATCGTTACTAGCTTGAAGTTGACCATCTG
GACGTACTTTCTGGTTTAGCCTCACAAGTGAGCAAGGAGGGTTGAGAGATGTGCTGT
GAGGAATGTGGGGCCCCAGCTGGCAGCAGGCTCTGGGTCAGGGGGGCAGGGACCACG
GGCATACCTGACAGTGAGGAGGGGTCTAGTAGGGATCAGTTCCCCTGTTGTTCTTT
AGAATTTTCTGGATATTCTTCTTTATTGATTTGGGATGTGAACAATAGAATCAACT
TCTACTTGTAGATTGATTTAGGGAGAACTTATACCTCAGATGTTAAGTCACCCTGTC
CAGAATGTGGGATGCTTTCCTATTTGTTCAGAACTTTTTAAATTACCTCAGAAGCAC
ATGAAATTTAAAGGATTTTAAAAAAAACTTAAAGATTATTTCACATAGCTCTTGCAC
ATTTCTTGATAAATGAATCCTCAGGTATTCCTCTGTTTTGTTACTAATAGTTACTT
CTTATGGGTTTTTTTTCCCCTGAAAATCATTTATCAAACGTATGTGGCTTATTTTCTG
AAGGATGTTTGATAATTTTGGAAGATATGAAAGTCTTCATATTTTACAAGGTTTGGG
GTCTCTTTAAGCTGCATGGTTCTCATGTCAGCTCCCAAAGCAGAAGACGGCATGTTG
AAAAATGCCGTAGAGAAGATACTTCTTTTCCACCTGTTTTCAACTCATATCATCTTG
AATTTCAGGGCACCTTTCCATGCTCCTAGTGCTTGCTATCTG

Figure 7B

```
TTTATTATTTTCCTTCCTGAATACCCTGAACTCCAGCATGTTCTGCTGTAATTCTGGC
CTCCCTGGCATCTTGGACTCCTGTTTCCTTTGCTCTGTCATCCCCGCGGTCAGCTCCT
GCTGCGCAGCTTCTCAGCTGAAGTGCGTTTGGAGTGCCTGGCGTGTCTTGCTGGATCT
TTGAGTATTGCCTCTGGTTTCCTTGGTTCCTTCTGCTGAGTTGCTCAGCGTCTCCACT
CCCCATTTCTTGTGTGGCCCTTCCTGCACTCCTCTGATTCCTTTTGTCTTCCCTGGTTT
CTTGCTTTGGTTTCGAGTCTCCACAGAACTTTTGCAGCTCTTCTGAAGACCTGGAAGC
TTTTTCATCTTAATTCTCATCTCATGACCTCTTTTCCCTTCTTTGAGAGCTAGAACTT
CCCATGGTGAACTTCTCTTTCCAGAATTCCATGCCTTCTTTTCCCTCCCACTTACCTG
TTGTCCAGGAGAGGTCAGATTGCTGTGCATATTGGAGGAGAACCCTTTCTTCCCTGG
GCTCTTCATCTCACATGACATCACCACATCACCTCGTTCCTTGGACCCTCAGTGGTGT
CACTGCTGGATTTTTCTTTCCTTTGGCTGGCCTTAGGGCACACCCAGGTTGACTAGCG
TAGTCATGGTATTTAGATCCACTCACATTTTCAGTTTCTGTGTCTGTCTCTTGCCTGC
TTCTGACTTCGCCCAGAGAAAGCTTCTCTTTCACAAGGGTTCTTAGATTTATGTTCAC
TGAGCACCTTCTTTTCTGAGGCAGTGTTTTACCAATATTTATTTTCCTAGTCAGTCTC
GCCTTACCTTTCTTGTTATGCATGTCTTTGGTCCTGACCCATTCTCTGAGTCTGTAAA
ATAGAATTGCTGTATAATTTAATTACATGAAATCCTTTAGAATCTTAACACATCTTA
CACCTGATTTAATATTTTATTGTATCCAAATTGAACCAACCCTATGTGAATTTGACA
GTGATTTCTCCCAGGGATCCTAGTGTATAAGGAATAGGACTTAGTATTTTCTATTTT
TTGATATACCACATACCAGATACTGATTATGATGGACATTTAACCCTTTTTTCTCAT
TATGAAAGAAAGTTAGGAATTATTTCTTCCAGTAGCGCCAGTGTAACCTGAAAGCCT
TTGAAAGAGTAGTTTTTGTATAGCTATCTGAAAGGAATTTCTTTCCAAAATATTTTT
CCAGTGCTGACAACAAACACGCAGACACACCCTGCAAGGTGAGTGTACGGCG
```

AAV2/1 mU6miHDS25IntronI/II 96.6% full virions
1.07E+13 vg/mL

Table 1

Table 1. % Packaging efficiencies of miR-intronI/II virions and % contaminants.

| | Cap/rAAV | Amp/rAAV | Gent/rAAV | Avg. Empty % | QPCR Titer (vg/mL) | Total vg/ml | Total # of (pt/ml) |
|---|---|---|---|---|---|---|---|
| AAV2/1mU6miSafeIntronI/II | 0.00% | 0.06% | 0.15% | 1.30% | 2.75E+13 | 2.76E+13 | 2.79E+13 |
| AAV2/1mU6miHDS26IntronI/II | 0.15% | 1.81% | 1.29% | 2.00% | 3.23E+12 | 3.34E+12 | 5.33E+12 |
| AAV2/1mU6miHDS26IntronI/II | 0.80% | 2.14% | 7.87% | 3.90% | 1.09E+13 | 1.22E+13 | 1.27E+13 |
| AAV2/1mU6miHDS25IntronI/II | 0.19% | 1.34% | 1.02% | 0.90% | 2.74E+12 | 2.81E+12 | 3.73E+12 |
| AAV2/1mU6miHDS25IntronI/II | 0.08% | 0.28% | 1.98% | 2.70% | 1.07E+13 | 1.09E+13 | 1.12E+13 |
| AAV2/1mU6miHDS10IntronI/II | 0.12% | 1.40% | 0.87% | 5.60% | 3.52E+12 | 3.60E+12 | 3.80E+12 |
| AAV2/1mU6miHDS1IntronI/II | 0.01% | 0.15% | 0.15% | 0.70% | 1.81E+13 | 1.82E+13 | 2.08E+13 |

MODIFIED ADENO-ASSOCIATED VIRUS VECTOR COMPOSITIONS

RELATED APPLICATIONS

This patent application claims the benefit of priority of U.S. Application Ser. No. 61/668,839, filed Jul. 6, 2012, which application is incorporated by reference herein.

SEQUENCE LISTING

The instant application contains a Sequence Listing which has been submitted in ASCII format via EFS-Web and is hereby incorporated by reference in its entirety. Said ASCII copy, created on Mar. 14, 2013, is named 17023.126WO1_SL.txt and is 39,125 bytes in size.

BACKGROUND

Adeno associated virus (AAV) is a small nonpathogenic virus of the parvoviridae family. AAV is distinct from the other members of this family by its dependence upon a helper virus for replication. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date many serologically distinct AAVs have been identified and have been isolated from humans or primates. Govindasamy et al., "Structurally Mapping the Diverse Phenotype of Adeno-Associated Virus Serotype 4," *J. Vir.*, 80 (23):11556-11570 (2006). For example, the genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner.

The following features of AAV have made it an attractive vector for gene transfer. AAV vectors possess a broad host range; transduce both dividing and non-dividing cells in vitro and in vivo and maintain high levels of expression of the transduced genes. Viral particles are heat stable, resistant to solvents, detergents, changes in pH, temperature, and can be concentrated on CsCl gradients. AAV is not associated with any pathogenic event, and transduction with AAV vectors has not been found to induce any lasting negative effects on cell growth or differentiation. The ITRs have been shown to be the only cis elements required for packaging allowing for complete gutting of viral genes to create vector systems.

There is a current need for AAV vectors that have improved packaging features.

SUMMARY

In certain embodiments, the present invention provides an adeno-associated virus (AAV) filler component (also called a "stuffer sequence") comprising a nucleic acid of between 3300 and 4200 nucleotides in length having at least 90% identity to SEQ ID NO:1 or SEQ ID NO:2.

In certain embodiments, the present invention provides an adeno-associated virus (AAV) filler component consisting of a nucleic acid of between 3300 and 4200 nucleotides in length having at least 90% identity to SEQ ID NO:1 or SEQ ID NO:2.

In certain embodiments, the present invention provides an AAV vector comprising the filler component described above.

BRIEF DESCRIPTION OF THE DRAWINGS AND TABLE

FIG. 1 is a plasmid map of 5pFBAAVmU6miHDS1stuffer (9110 bp).

FIGS. 2A-2R collectively provide the sequence of 5pFBAAVmU6miHDS1stuffer (Stuffer #1) (SEQ ID NO:3).

FIGS. 3A-3C provide the sequences of the various individual components of 5pFBAAVmU6miHDS1stuffer (SEQ ID NO:1, 4-11).

FIGS. 6A-6D collectively provide the plasmid sequence for 5pFBAAVmU6miHDS1-stuffer (SEQ ID NO:12).

FIGS. 7A-7B collectively provide a stuffer sequence (Stuffer #2) (SEQ ID NO:2).

Figure 8:
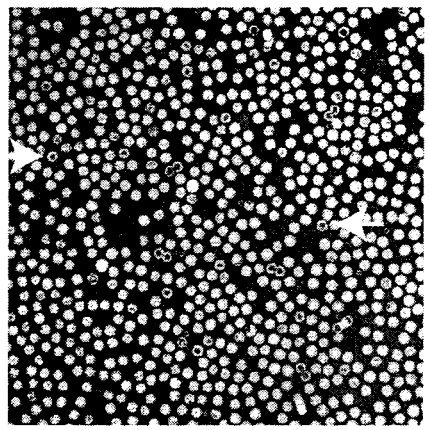

FIG. 8. EM evaluation of full virions vs. empty virions. Two examples of empty virions are highlighted by the arrows. This prep had only ~4% empty virions, which is quite low.

Figure 9:
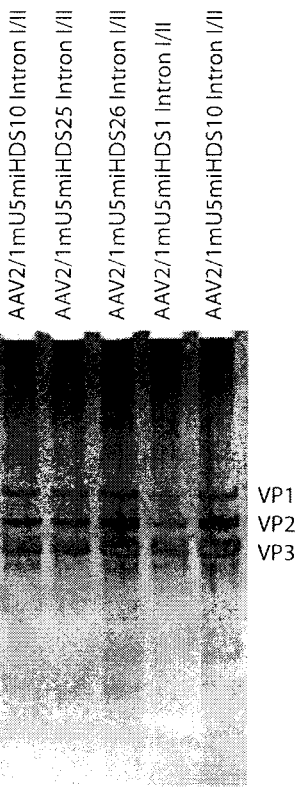

FIG. 9. Silver stain to examine the capsid integrity of the purified virions. Several different miRNA-expressing constructs were engineered into the shuttle vector along with the intron I/II stuffer to generate near wild type genome size. The purified viruses show optimal VP1, VP2 and VP3 protein ratios.

Table 1. % Packaging efficiencies of miR-intronI/II virions and % contaminants.

DETAILED DESCRIPTION

AAV Vectors and Expression Cassettes

The viral vectors of the invention utilize an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV-1 to AAV-8. For example, serotype AAV-2 is used to refer to an AAV which contains capsid proteins encoded from the cap gene of AAV-2 and a genome containing 5' and 3' ITR sequences from the same AAV-2 serotype.

Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped rAAV are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2.

The abbreviation "rAAV" refers to recombinant adeno-associated virus, also referred to as a recombinant AAV vector (or "rAAV vector"). In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector.

AAV ITRs can be excised from an AAV vector plasmid containing the same and fused 5' and 3' of a selected nucleic acid construct that is present in another vector using standard ligation techniques, such as those described in Sambrook and Russell, Molecular Cloning: A Laboratory Manual, Cold Spring Harbor Laboratory Press Cold Spring Harbor, N.Y. (2001). For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

The adeno-associated virus preferentially packages a full-length genome, i.e., one that is approximately the same size as the native genome, and is not too big or too small. Many target nucleic acid sequences, or expression cassettes encoding target nucleic acid sequences, are very small. To avoid packaging of fragmented genomes, the present inventors designed and tested a nucleic acid sequence when linked to an expression cassette, resulted in a genome whose size was near-normal in length between the ITRs. The starting sequence was of mammalian origin, but was significantly modified to ensure that this "filler component" (also called a "stuffer sequence") was devoid of enhancers, promoters, splicing regulators, noncoding RNAs or antisense sequences, among other things. In other words, the stuffer sequences are "silent" and confer no activity to the expression cassette.

In the present invention, suitable DNA molecules for use in AAV vectors will include, for example, a stuffer sequence and an expression cassette encoding a siRNA molecule of the invention. Many expression cassettes are very small, for example, those expressing inhibitory RNAs (siRNAs and shRNAs). Thus, there is a need to add sequences to the cassette such that it makes up a full-length or near full-length AAV genome. If only the small genome was used in the AAV production, the recombinant virions would be heterogeneous and contain various size genomes. This is because the virus likes to package full length genomes so it would pick up other DNA fragments to fill that space. The stuffer cannot be too big, as AAV genomes above 105% of the wild-type genome size will generally not be packaged.

In certain embodiments, the present invention provides an adeno-associated virus (AAV) filler component (also called a "stuffer sequence") comprising a nucleic acid of between 3300 and 4200 nucleotides in length having at least 90% identity to SEQ ID NO:1 or SEQ ID NO:2.

(SEQ ID NO: 1)
```
GAATTCGGGCTATCCCAGGTTGCCTTGGTTCATGGCAAATGGGACGTTAAGAGGGCAGAGAGAAT

ATGAACAGAAACTGTTCTAATATTGGTCATTTAATGTGTAAGTATTGTTCTTTTTTAAACCTCCTTC

ATTTTTTTTCCAGGAATTGCTGGACACAGTGGCTTGGTGTGTGTCTGAGGACTGTAGGCCATGGCC

CTAGGTTGTGGTTTTAGGTCTCAGGTGCTCTTCCTGGCTGTCTCCTTGCTTCTTTCCCATGTCCTCTT

CTTTGTTTCCAGCCATTTCTCCCTTATGCTTAAGTTTGGTGCAGCAGGGTTTGGCTGCTCTCAGATT

CCTGCTTCCTCAGATGCTGTAGTTGTCAGGCCCAGCGGGCTGGCAGCGGGATCAGGATCTGGCTAG

GTTTGCTCTCACTGTGGCAGAGTAGGGGGAGGCGTGGGAGAGCACGTGTGACCCCAGGCCAGCTG

TAGGGAGCATAGGCATGGTCACGTAGCCTTCAGGTCCTAGACTTTGTCTTCTCATGAGTATGGCTG

TGTGTGTATGGTGAAAACTAGGTTCTACTTAGCCCAAGAAAATGGGCACATTTTGCATGTGGTTTC
```

-continued

```
TGTAGAGAAATGCACTGGGTATCTGACATAGCCTGGCAGCATGCCTCCCTCAGGTAGGTTAGTCTC

AGGCGGTGAAGCACGTGTGTCCAGCAAGAACTTCATATGTGGCATAAAGTCTCCGTTCTGTGAGGT

GCTGGCAAATCACCACCACCGTCAAGAGGCTGAAGTGATTTTTGTCTAGGGAGGCAGGAAAGGCT

TCCTGGAGTCAGCAGCCAGTAGGTGAAAGAGTAGATTGGAGACCTTCTTAATCATCACCGCCTCTT

GTCTCAAGGGGTGCCAGGAAGCTGTGGAGGCTGAACCCATCTTATGCTGCCAGAGAGTGGGACAC

CATGAGGGTCAGGTCAAGGGGTTGTACCTTGTTTGGTAGAGAATTAGGGGCTCTTGAAGACTTTGG

ATGTGGTCAGGGGAGTGTATCATTTAGGAAGAGTGACCCGGTGAGGACGTGGGGTAGAGGAGGAC

AGGTGGGAGGGAGTCCAGGTGGGAGTGAGTAGACCCAGCAGGAGTGCAGGGCCTCGAGCCAGGA

TGGTGGCAGGGCTGTGAGGAGAGGCAGCCACCTGTGTGTCTGCGGAAGCAGGGGCAAGAGGGAA

GAGGCCAGCAGCGTGCTGCCATCACCCAGCGACTGGCGTAGATTGTGAGAGACCATTCCCTGCTCT

TAGGAGGGGCTGAGTTTTAGTTTTCTCTTGTTATACAATAAGCTTGGTATTTGTTTACAAAACATTT

GTAAAGCTAAATCAAGGTTTGATAAGGCTTCTAGTTTTATTTAAGAAGTAATGTTGAAATAAATGT

TTGTCCAATTCGCTTTGCTCATTTAAGGACTTTCAGTACAAACTGCAACAACAGGATTAGGATTTA

AACGTTTCTGAGATGTTTTTACTCCTCAGAATTTCCCAGAATGTGATCTGGTTTTGATTTTCAAGCT

TGCTGACCCAATAGGTTAACCCACAAGTTTTACGAAGACCATCTCAGTCCACTTACATCAACTGCC

CATGCCACGGTTAAAGAGATCATCGACTGATGTTTGGCACAGCTTCCTCCCTCTTGGGTGGGCAAG

CATTTGGAAGAGAAGGCTCCTATGGGTGAGAGTGGGGCACCAAAGTCTTCCCTGTCCCATCCCCTA

GCTTGAGAAGCCCTTCTCTAATGTGGACTTTGTGCCGTTAGCATCGTTACTAGCTTGAAGTTGACCA

TCTGGACGTACTTTCTGGTTTAGCCTCACAAGTGAGCAAGGAGGGTTGAGAGATGTGCTGTGAGGA

ATGTGGGCCCCAGCTGGCAGCAGGCTCTGGGTCAGGGGGCAGGGACCACGGGCATACCTGACA

GTGAGGAGGGTCTAGTAGGGGATCAGTTCCCCTGTTGTTCTTTAGAATTTTCTGGATATTCTTCTTT

ATTGATTTTGGGATGTGAACAATAGAATCAACTTCTACTTGTAGATTGATTTAGGGAGAACTTATA

CCTCAGATGTTAAGTCACCCTGTCCAGAATGTGGGATGCTTTCCTATTTGTTCAGAACTTTTTAAAT

TACCTCAGAAGCACATGAAATTTAAAGGATTTTAAAAAAAACTTAAAGATTATTTCACATAGCTCT

TGCACATTTCTTGATAAATGAATCCTCAGGTATTCCTCTGTTTTTGTTACTAATAGTTACTTCTTATG

GGTTTTTTTTCCCCTGAAAATCATTTATCAAACGTATGTGGCTTATTTTCTGAAGGATGTTTGATAA

TTTTGGAAGATATGAAAGTCTTCATATTTTACAAGGTTTGAGGTCTCTTTAAGCTGCATGGTTCTCA

TGTCAGCTCCCAAAGCAGAAGACGGCATGTTGAAAAATGCCGTAGAGAAGATACTTCTTTTCCACC

TGTTTTCAACTCATATCATCTTGAATTTCAGGGCACCITTCCATGCTCCTAGTGCTTGCTATCTGTTT

ATTATTTTCCTTCCTGAATACCCTGAACTCCAGCATGTTCTGCTGTAATTCTGGCCTCCCTGGCATC

TTGGACTCCTGTTTCCTTTGCTCTGTCATCCCCGCGGTCAGCTCCTGCTGCGCAGCTTCTCAGCTGA

AGTGCGTTTGGAGTGCCTGGCGTGTCTTGCTGGATCTTTGAGTATTGCCTCTGGTTTCCTTGGTTCC

TTCTGCTGAGTTGCTCAGCGTCTCCACTCCCCATTTCTTGTGTGGCCCTTCCTGCACTCCTCTGATTC

CTTTTGTCTTCCCTGGTTTCTTGCTTTGGTTTCGAGTCTCCACAGAACTTTTGCAGCTCTTCTGAAGA

CCTGGAAGCTTTTTCATCTTAATTCTCATCTCATGACCTCTTTTCCCTTCTTTGAGAGCTAGAACTTC

CCATGGTGAACTTCTCTTTCCAGAATTCCATGCCTTCTTTTCCCTCCCACTTACCTGTTGTCCAGGA

GAGGTCAGATTGCTGTGCATATTGGAGGAGAACCCTTTCTTCCCTGGGCTCTTCATCTCACATGAC

ATCACCACATCACCTCGTTCCTTGGACCCTCAGTGGTGTCACTGCTGGATTTTTCTTTCCTTTGGCT

GGCCTTAGGGCACACCCAGGTTGACTAGCGTAGTCATGGTATTTAGATCCACTCACATTTTCAGTT

TCTGTGTCTGTCTCTTGCCTGCTTCTGACTTCGCCCAGAGAAAGCTTCTCTTTCACAAGGGTTCTTA

GATTTATGTTCACTGAGCACCTTCTTTTCTGAGGCAGTGTTTTACCAATATTTATTTTCCTAGTCAGT
```

-continued

```
CTCGCCTTACCTTTCTTGTTATGCATGTCTTTGGTCCTGACCCATTCTCTGAGTCTGTAAAATAGAA
TTGCTGTATAATTTAATTACATGAAATCCTTTAGAATCTTAACACATCTTACACCTGATTTAATATT
TTATTGTATCCAAATTGAACCAACCCTATGTGAATTTGACAGTGATTTCTCCCAGGGATCCTAGTGT
ATAAGGAATAGGACTTAGTATTTTCTATTTTTTGATATACCACATACCAGATACTGATTATGATGG
ACATTTAACCCTTTTTTCTCATTATGAAAGAAAGTTAGGAATTATTTCTTCCAGTAGCGCCAGTGTA
ACCTGAAAGCCTTTGAAAGAGTAGTTTTTGTATAGCTATCTGAAAGGAATTTCTTTCCAAAATATTT
TTCCAGTGCTGACAACAAACACGCAGACACACCCTGCAAGGTGAGTGTACGGCG
```

(SEQ ID NO: 2)
```
GGGCTATCCCAGGTTGCCTTGGTTCATGGCAAATGGGACGTTAAGAGGGCAGAGAGAATATGAAC
AGAAACTGTTCTAATATTGGTCATTTAATGTGTAAGTATTGTTCTTTTTTAAACCTCCTTCATTTTTT
TTCCAGGAATTGCTGGACACAGTGGCTTGGTGTGTGTCTGAGGACTGTAGGCCATGGCCCTAGGTT
GTGGTTTTAGGTCTCAGGTGCTCTTCCTGGCTGTCTCCTTGCTTCTTTCCCATGTCCTCTTCTTTGTTT
CCAGCCATTTCTCCCTTATGCTTAAGTTTGGTGCAGCAGGGTTTGGCTGCTCTCAGATTCCTGCTTC
CTCAGATGCTGTAGTTGTCAGGCCCAGCGGGCTGGCAGCGGGATCAGGATCTGGCTAGGTTTGCTC
TCACTGTGGCAGAGTAGGGGGAGGCGTGGGAGAGCACGTGTGACCCCAGGCCAGCTGTAGGGAG
CATAGGCATGGTCACGTAGCCTTCAGGTCCTAGACTTTGTCTTCTCATGAGTATGGCTGTGTGTA
TGGTGAAAACTAGGTTCTACTTAGCCCAAGAAAATGGGCACATTTTGCATGTGGTTTCTGTAGAGA
AATGCACTGGGTATCTGACATAGCCTGGCAGCATGCCTCCCTCAGGTAGGTTAGTCTCAGGCGGTG
AAGCACGTGTGTCCAGCAAGAACTTCATATGTGGCATAAAGTCTCCGTTCTGTGAGGTGCTGGCAA
ATCACCACCACCGTCAAGAGGCTGAAGTGATTTTTGTCTAGGGAGGCAGGAAAGGCTTCCTGGAG
TCAGCAGCCAGTAGGTGAAAGAGTAGATTGGAGACCTTCTTAATCATCACCGCCTCTTGTCTCAAG
GGGTGCCAGGAAGCTGTGGAGGCTGAACCCATCTTATGCTGCCAGAGAGTGGGACACCATGAGGG
TCAGGTCAAGGGGTTGTACCTTGTTTGGTAGAGAATTAGGGGCTCTTGAAGACTTTGGATGTGGTC
AGGGGAGTGTATCATTTAGGAAGAGTGACCCGGTGAGGACGTGGGGTAGAGGAGGACAGGTGGG
AGGGAGTCCAGGTGGGAGTGAGTAGACCCAGCAGGAGTGCAGGGCCTCGAGCCAGGATGGTGGC
AGGGCTGTGAGGAGAGGCAGCCACCTGTGTGTCTGCGGAAGCAGGGCAAGAGGGAAGAGGCCA
GCAGCGTGCTGCCATCACCCAGCGACTGGCGTAGATTGTGAGAGACCATTCCCTGCTCTTAGGAGG
GGCTGAGTTTTAGTTTTCTCTTGTTATACAATAAGCTTGGTATTTGTTTACAAAACATTTGTAAAGC
TAAATCAAGGTTTGATAAGGCTTCTAGTTTTATTTAAGAAGTAATGTTGAAATAAATGTTTGTCCA
ATTCGCTTTGCTCATTTAAGGACTTTCAGTACAAACTGCAACAACAGGATTAGGATTTAAACGTTT
CTGAGATGTTTTTACTCCTCAGAATTTCCCAGAATGTGATCTGGTTTTGATTTTCAAGCTTGCTGAC
CCAATAGGTTAACCCACAAGTTTTACGAAGACCATCTCAGTCCACTTACATCAACTGCCCATGCCA
CGGTTAAAGAGATCATCGACTGATGTTTGGCACAGCTTCCTCCCTCTTGGGTGGGCAAGCATTTGG
AAGAGAAGGCTCCTATGGGTGAGAGTGGGGCACCAAAGTCTTCCCTGTCCCATCCCCTAGCTTGAG
AAGCCCTTCTCTAATGTGGACTITGTGCCGTTAGCATCGTTACTAGCTTGAAGTTGACCATCTGGAC
GTACTTTCTGGTTTAGCCTCACAAGTGAGCAAGGAGGGTTGAGAGATGTGCTGTGAGGAATGTGG
GGCCCCAGCTGGCAGCAGGCTCTGGGTCAGGGGGCAGGGACCACGGGCATACCTGACAGTGAG
GAGGGGTCTAGTAGGGGATCAGTTCCCCTGTTGTTCTTTAGAATTTTCTGGATATTCTTCTTTATTG
ATTTTGGGATGTGAACAATAGAATCAACTTCTACTTGTAGATTGATTTAGGGAGAACTTATACCTC
AGATGTTAAGTCACCCTGTCCAGAATGTGGGATGCTTTCCTATTTGTTCAGAACTTTTTAAATTACC
TCAGAAGCACATGAAATTTAAAGGATTTTAAAAAAAACTTAAAGATTATTTCACATAGCTCTTGCA
```

-continued

```
CATTTCTTGATAAATGAATCCTCAGGTATTCCTCTGTTTTTGTTACTAATAGTTACTTCTTATGGGTT

TTTTTTCCCCTGAAAATCATTTATCAAACGTATGTGGCTTATTTTCTGAAGGATGTTTGATAATTTT

GGAAGATATGAAAGTCTTCATATTTTACAAGGTTTGGGGTCTCTTTAAGCTGCATGGTTCTCATGTC

AGCTCCCAAAGCAGAAGACGGCATGTTGAAAAATGCCGTAGAGAAGATACTTCTTTTCCACCTGTT

TTCAACTCATATCATCTTGAATTTCAGGGCACCTTTCCATGCTCCTAGTGCTTGCTATCTGTTTATTA

TTTTCCTTCCTGAATACCCTGAACTCCAGCATGTTCTGCTGTAATTCTGGCCTCCCTGGCATCTTGG

ACTCCTGTTTCCTTTGCTCTGTCATCCCCGCGGTCAGCTCCTGCTGCGCAGCTTCTCAGCTGAAGTG

CGTTTGGAGTGCCTGGCGTGTCTTGCTGGATCTTTGAGTATTGCCTCTGGTTTCCTTGGTTCCTTCTG

CTGAGTTGCTCAGCGTCTCCACTCCCCATTTCTTGTGTGGCCCTTCCTGCACTCCTCTGATTCCTTTT

GTCTTCCCTGGTTTCTTGCTTTGGTTTCGAGTCTCCACAGAACTTTTGCAGCTCTTCTGAAGACCTG

GAAGCTTTTTCATCTTAATTCTCATCTCATGACCTCTTTTCCCTTCTTTGAGAGCTAGAACTTCCCAT

GGTGAACTTCTCTTTCCAGAATTCCATGCCTTCTTTTCCCTCCCACTTACCTGTTGTCCAGGAGAGG

TCAGATTGCTGTGCATATTGGAGGAGAACCCTTTCTTCCCTGGGCTCTTCATCTCACATGACATCAC

CACATCACCTCGTTCCTTGGACCCTCAGTGGTGTCACTGCTGGATTTTTCTTTCCTTTGGCTGGCCTT

AGGGCACACCCAGGTTGACTAGCGTAGTCATGGTATTTAGATCCACTCACATTTTCAGTTCTGTGT

CTGTCTCTTGCCTGCTTCTGACTTCGCCCAGAGAAAGCTTCTCTTTCACAAGGGTTCTTAGATTTAT

GTTCACTGAGCACCTTCTTTTCTGAGGCAGTGTTTTACCAATATTTATTTTCCTAGTCAGTCTCGCCT

TACCTTTCTTGTTATGCATGTCTTTGGTCCTGACCCATTCTCTGAGTCTGTAAAATAGAATTGCTGT

ATAATTTAATTACATGAAATCCTTTAGAATCTTAACACATCTTACACCTGATTTAATATTTTATTGT

ATCCAAATTGAACCAACCCTATGTGAATTTGACAGTGATTTCTCCCAGGGATCCTAGTGTATAAGG

AATAGGACTTAGTATTTTCTATTTTTTGATATACCACATACCAGATACTGATTATGATGGACATTTA

ACCCTTTTTCTCATTATGAAAGAAAGTTAGGAATTATTTCTTCCAGTAGCGCCAGTGTAACCTGAA

AGCCTTTGAAAGAGTAGTTTTTGTATAGCTATCTGAAAGGAATTTCTTTCCAAAATATTTTTCCAGT

GCTGACAACAAACACGCAGACACACCCTGCAAGGTGAGTGTACGGCG
```

In certain embodiments, the present invention provides an adeno-associated virus (AAV) filler component consisting of a nucleic acid of between 3300 and 4200 nucleotides in length having at least 90% identity to SEQ ID NO:1 or SEQ ID NO:2. In certain embodiments, the filler component consists of at least 90% identity with SEQ ID NO:1 or SEQ ID NO:2. In certain embodiments, the filler component has 95% identity, 98% identity, 99% identity, or even 100% identity with SEQ ID NO:1 or SEQ ID NO:2. In certain embodiments, the filler component has a length of about 3500-4000 nucleotides, or of about 3700-3850 nucleotides. In the present invention, the filler component is "silent" in terms of biological activity, in that it is devoid of enhancers, promoters, splicing regulators, noncoding RNAs, antisense sequences, or coding sequences.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host.

AAV ITRs

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision from plasmids expressing them.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a vector, and to package the desired genome into the AAV virion.

In one embodiment, AAV ITRs can be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a vector, and to allow packaging of the desired genome into the AAV virion.

In certain embodiments, the present invention provides an adeno-associated virus (AAV) vector comprising the filler component as described above operably linked to an expression cassette. In certain embodiments, the expression cassette comprises a promoter. In certain embodiments, the promoter is a pol III promoter. In certain embodiments, the promoter is a mU6 promoter. In certain embodiments, the AAV vector further comprising a target sequence. In certain embodiments, the target sequence is an RNAi molecule.

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNAi molecule. The expression cassette including the nucleotide sequence of interest may be chimeric. The expression cassette may also be one that is naturally occurring but has been obtained in a recombinant form useful for heterologous expression.

Double-stranded RNA (dsRNA) can induce sequence-specific posttranscriptional gene silencing in many organisms by a process known as RNA interference (RNAi). RNA fragments are the sequence-specific mediators of RNAi. Interference of gene expression by these RNA interference (RNAi) molecules is now recognized as a naturally occurring strategy for silencing genes in the cells of many organisms.

Certain embodiments of the present invention provide a vector that encodes an isolated RNAi molecule. As used herein the term "encoded by" is used in a broad sense, similar to the term "comprising" in patent terminology. RNAi molecules include siRNAs, shRNAs and other small RNAs that can or are capable of modulating the expression of a target gene, for example via RNA interference. Such small RNAs include without limitation, shRNAs and miroRNAs (miRNAs).

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The invention will now be illustrated by the following non-limiting Examples.

Example 1

Figure 1:
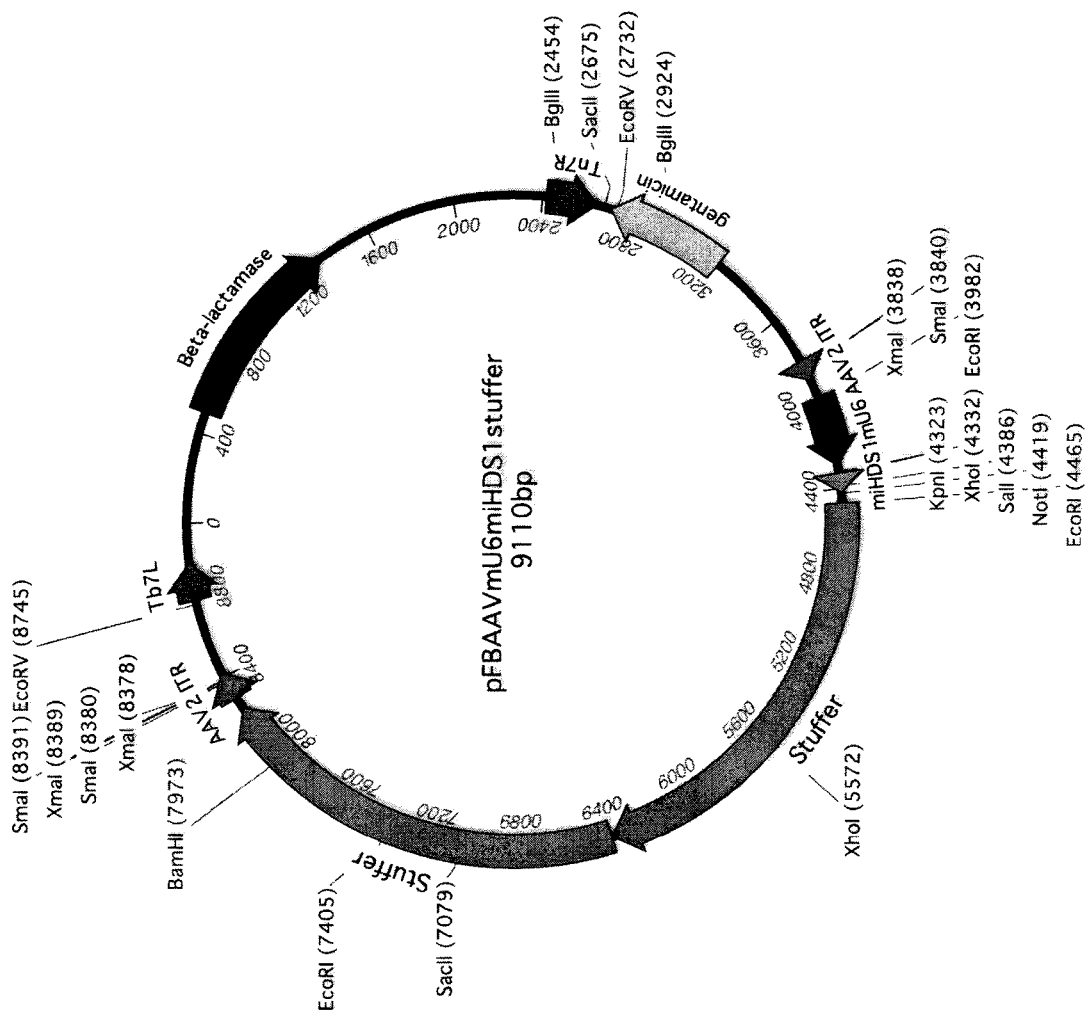
Figure 2R:
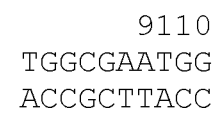

A plasmid FBAAVmU6miHDS1 stuffer was generated that included AAV2 ITRs, mU6 promoter, miHDS1 target sequence, filler component stuffer, and an AAV backbone (FIG. 1). The sequence for 5pFBAAVmU6miHDS1 AAVstuffer is provided in FIG. 2, and the sequences for the individual components of the plasmid are provided in FIG. 3. The full-length filler component ("stuffer sequence") consisted of 3776 nucleotides.

Example 2

The in vivo silencing efficiency of a vectors expressing miHDS1 was compared. Four vectors were constructed: (1) a vector expressing a control sequence (miSAFE) and containing a control sequence (eGFP), (2) a vector expressing the target sequence (miHDS1) and containing a control sequence (eGFP), (3) a vector expressing a control sequence (miSAFE) and containing the stuffer sequence described in Example 1, and (4) a vector expressing the target sequence (miHDS1) and containing the stuffer sequence described in Example 1.
 (1) AAV2/1 mU6miSAFE-eGFP (4.81E12 µg/ml)
 (2) AAV2/1 mU6miHDS1-eGFP (4.81E12 µg/ml)
 (3) AAV2/1 mU6miSAFE-stuffer (4.81E12 µg/ml)
 (4) AAV2/1 mU6miHDS1-stuffer (4.81E12 µg/ml)

Figure 4:
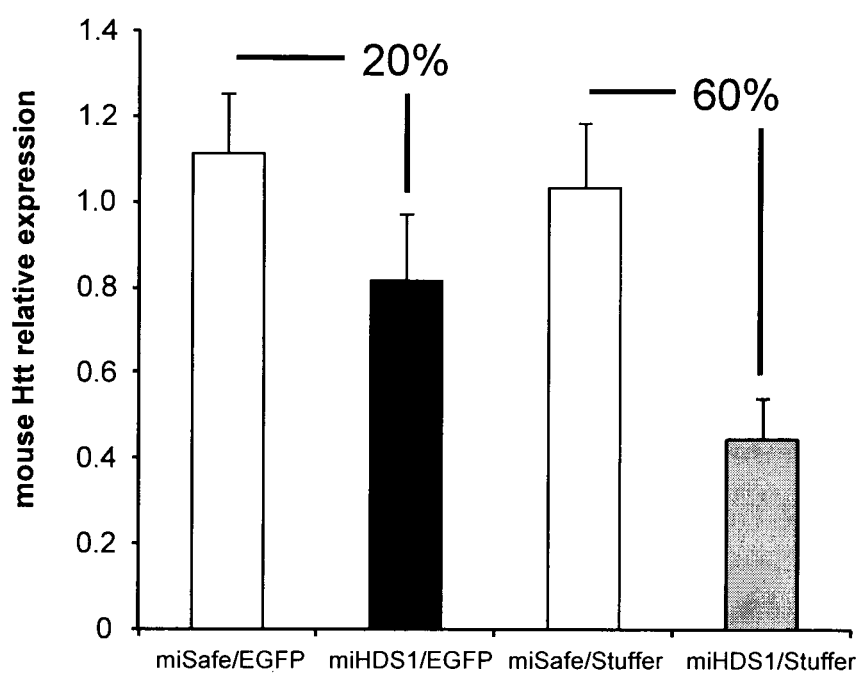
FIG. 4 is a graph showing relative Htt expression.

The sequences for miSAFE and miHDS1 have been previously discussed (see, PCT/US2012/024904, which is hereby incorporated by reference herein in its entirety). Wild type mice were injected in the striatum with the four vectors. Mice were sacrificed one month later and Htt expression was determined relative to Actb expression levels by QPCR. FIG. 4 shows that there was a 20% decrease in expression between the misafe/eGFP and the miHDS1/eGFP expression cassettes, whereas there was a 60% decrease in expression between the misafe/stuffer and the miHDS1/stuffer expression cassettes, i.e., a 60% decrease in expression when the stuffer was used.

Example 3

Figure 5:
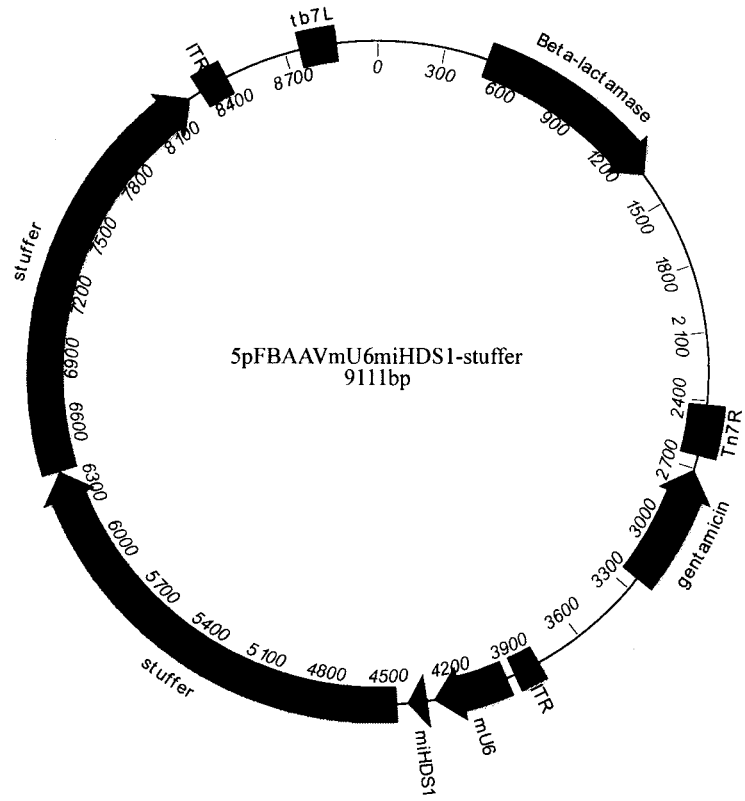
FIG. 5 is a plasmid map of 5pFBAAVmU6miHDS1-stuffer.

A plasmid 5pFBAAVmU6miHDS1stuffer was generated that included AAV2 ITRs, mU6 promoter, miHDS1 target sequence, filler component stuffer, and an AAV backbone (FIG. 5). The sequence for the plasmid 5pFBAAVmU6miHDS1AAV-stuffer is provided in FIG. 6. The sequence for the stuffer (Stuffer #2) is provided in FIG. 7.

Example 4

One of the considerations with AAV packaging is maintaining optimal genome size. When this occurs, the ratio of virions that form which are lacking genomes are minimized. Experiments were performed testing the packaging efficiency of the new stuffer sequences and found high efficiency packaging. For example, see Table 1 "Average empty" and FIG. 8). It was also measured if genetic material that was packaged contained non-miRNA:intron stuffer sequences. It was found that the incorporation of unintended genomic material used in virus production was extremely low (Cap/rAAV, Amp/rAAV, Gent/rAAV). Finally, the quality of the viruses were analyzed by Silver Stain after polyacrylamide gel electrophoresis and found to contain the appropriate proportions of the various capsid proteins (VP1, VP2, and VP3; FIG. 9). In summary, the intron I/II stuff sequence allows optimal packaging of desired transgenes into AAV capsids.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An adeno-associated virus (AAV) filler component comprising a nucleic acid having at least 90% identity to SEQ ID NO:1 or SEQ ID NO:2, wherein the nucleic acid is between 3500 and 4000 nucleotides.

2. An adeno-associated virus (AAV) filler component consisting of a nucleic acid having at least 90% identity to SEQ ID NO:1 or SEQ ID NO:2.

3. The AAV filler component of claim 2, wherein the nucleic acid is between 3500 and 4000 nucleotides.

4. The AAV filler component of claim 1, wherein the nucleic acid is between 3700 and 3850 nucleotides.

5. A recombinant adeno-associated virus (AAV) vector comprising the filler component of claim 1 operably linked to an expression cassette, wherein the AAV vector is approximately 5 kb in length.

6. The AAV vector of claim 5, wherein the expression cassette comprises a promoter.

7. The AAV vector of claim 6, wherein the promoter is a pol III promoter.

8. The AAV vector of claim 7, wherein the promoter is a mU6 promoter.

9. The AAV vector of claim 5, further comprising a target sequence.

10. The AAV vector of claim 9, wherein the target sequence is an RNAi molecule.

11. The AAV vector of claim 5, wherein the AAV vector is an AAV1, AAV2, AAV3, AAV4, AAV5, AAV6, AAV7, or AAV8 serotype.

12. The AAV vector of claim 5, further comprising an inverted terminal repeat (ITR) of any one of serotype AAV1, AAV2, AAV3, AAV4, AAV5, AAV6, AAV7, or AAV8.

13. The AAV filler component of claim 1, wherein the nucleic acid has at least 95% identity to SEQ ID NO:1 or SEQ ID NO:2.

14. The AAV filler component of claim 1, wherein the nucleic acid has at least 98% identity to SEQ ID NO:1 or SEQ ID NO:2.

15. The AAV filler component of claim 1, wherein the nucleic acid has at least 99% identity to SEQ ID NO:1 or SEQ ID NO:2.

16. The AAV filler component of claim 2, wherein the nucleic acid has at least 95% identity to SEQ ID NO:1 or SEQ ID NO:2.

17. The AAV filler component of claim 2, wherein the nucleic acid has at least 98% identity to SEQ ID NO:1 or SEQ ID NO:2.

18. The AAV filler component of claim 2, wherein the nucleic acid has at least 99% identity to SEQ ID NO:1 or SEQ ID NO:2.

* * * * *

SEQUENCE LISTING

<160> NUMBER OF SEQ ID NOS: 12

<210> SEQ ID NO 1
<211> LENGTH: 3774
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

| | | | | | |
|---|---|---|---|---|---|
| gaattcgggc | tatcccaggt | tgccttggtt | catggcaaat | gggacgttaa | gagggcagag | 60 |
| agaatatgaa | cagaaactgt | tctaatattg | gtcatttaat | gtgtaagtat | tgttcttttt | 120 |
| taaacctcct | tcatttttt | tccaggaatt | gctggacaca | gtggcttggt | gtgtgtctga | 180 |
| ggactgtagg | ccatggccct | aggttgtggt | tttaggtctc | aggtgctctt | cctggctgtc | 240 |
| tccttgcttc | tttcccatgt | cctcttcttt | gtttccagcc | atttctccct | tatgcttaag | 300 |
| tttggtgcag | cagggtttgg | ctgctctcag | attcctgctt | cctcagatgc | tgtagttgtc | 360 |
| aggcccagcg | ggctggcagc | gggatcagga | tctggctagg | tttgctctca | ctgtggcaga | 420 |
| gtagggggag | gcgtgggaga | gcacgtgtga | ccccaggcca | gctgtaggga | gcataggcat | 480 |
| ggtcacgtag | ccttcaggtc | ctagactttg | tcttctcatg | agtatggctg | tgtgtgtatg | 540 |
| gtgaaaacta | ggttctactt | agcccaagaa | aatgggcaca | ttttgcatgt | ggtttctgta | 600 |
| gagaaatgca | ctgggtatct | gacatagcct | ggcagcatgc | ctccctcagg | taggttagtc | 660 |
| tcaggcggtg | aagcacgtgt | gtccagcaag | aacttcatat | gtggcataaa | gtctccgttc | 720 |
| tgtgaggtgc | tggcaaatca | ccaccaccgt | caagaggctg | aagtgatttt | tgtctaggga | 780 |
| ggcaggaaag | gcttcctgga | gtcagcagcc | agtaggtgaa | agagtagatt | ggagaccttc | 840 |
| ttaatcatca | ccgcctcttg | tctcaagggg | tgccaggaag | ctgtggaggc | tgaacccatc | 900 |
| ttatgctgcc | agagagtggg | acaccatgag | ggtcaggtca | aggggttgta | ccttgtttgg | 960 |
| tagagaatta | ggggctcttg | aagactttgg | atgtggtcag | gggagtgtat | catttaggaa | 1020 |
| gagtgacccg | gtgaggacgt | ggggtagagg | aggacaggtg | ggagggagtc | caggtgggag | 1080 |
| tgagtagacc | cagcaggagt | gcagggcctc | gagccaggat | ggtggcaggg | ctgtgaggag | 1140 |
| aggcagccac | ctgtgtgtct | gcggaagcag | gggcaagagg | gaagaggcca | gcagcgtgct | 1200 |
| gccatcaccc | agcgactggc | gtagattgtg | agagaccatt | ccctgctctt | aggaggggct | 1260 |
| gagttttagt | tttctcttgt | tatacaataa | gcttggtatt | tgtttacaaa | acatttgtaa | 1320 |
| agctaaatca | aggtttgata | aggcttctag | ttttatttaa | gaagtaatgt | tgaaataaat | 1380 |
| gtttgtccaa | ttcgctttgc | tcatttaagg | actttcagta | caaactgcaa | caacaggatt | 1440 |
| aggatttaaa | cgtttctgag | atgttttac | tcctcagaat | tcccagaat | gtgatctggt | 1500 |
| tttgattttc | aagcttgctg | acccaatagg | ttaacccaca | agttttacga | agaccatctc | 1560 |
| agtccactta | catcaactgc | ccatgccacg | gttaaagaga | tcatcgactg | atgtttggca | 1620 |
| cagcttcctc | cctcttgggt | gggcaagcat | ttggaagaga | aggctcctat | gggtgagagt | 1680 |
| ggggcaccaa | agtcttccct | gtcccatccc | ctagcttgag | aagcccttct | ctaatgtgga | 1740 |
| ctttgtgccg | ttagcatcgt | tactagcttg | aagttgacca | tctggacgta | ctttctggtt | 1800 |
| tagcctcaca | agtgagcaag | gagggttgag | agatgtgctg | tgaggaatgt | ggggcccag | 1860 |
| ctggcagcag | gctctgggtc | aggggggcag | ggaccacggg | catacctgac | agtgaggagg | 1920 |
| gtctagtagg | ggatcagttc | ccctgttgtt | ctttagaatt | ttctgatat | tcttctttat | 1980 |

```
tgattttggg atgtgaacaa tagaatcaac ttctacttgt agattgattt agggagaact      2040
tatacctcag atgttaagtc accctgtcca gaatgtggga tgctttccta tttgttcaga      2100
actttttaaa ttacctcaga agcacatgaa atttaaagga ttttaaaaaa aacttaaaga      2160
ttatttcaca tagctcttgc acatttcttg ataaatgaat cctcaggtat tcctctgttt      2220
ttgttactaa tagttacttc ttatgggttt tttttcccct gaaaatcatt tatcaaacgt      2280
atgtggctta ttttctgaag gatgtttgat aattttggaa gatatgaaag tcttcatatt      2340
ttacaaggtt tgaggtctct ttaagctgca tggttctcat gtcagctccc aaagcagaag      2400
acggcatgtt gaaaaatgcc gtagagaaga tacttctttt ccacctgttt tcaactcata      2460
tcatcttgaa tttcagggca ccttttccatg ctcctagtgc ttgctatctg tttattattt      2520
tccttcctga ataccctgaa ctccagcatg ttctgctgta attctggcct ccctggcatc      2580
ttggactcct gtttcctttg ctctgtcatc cccgcggtca gctcctgctg cgcagcttct      2640
cagctgaagt gcgtttggag tgcctggcgt gtcttgctgg atctttgagt attgcctctg      2700
gtttccttgg ttccttctgc tgagttgctc agcgtctcca ctccccattt cttgtgtggc      2760
ccttcctgca ctcctctgat tccttttgtc ttccctggtt tcttgctttg gtttcgagtc      2820
tccacagaac ttttgcagct cttctgaaga cctggaagct ttttcatctt aattctcatc      2880
tcatgacctc ttttcccttc tttgagagct agaacttccc atggtgaact tctctttcca      2940
gaattccatg ccttcttttc cctcccactt acctgttgtc caggagaggt cagattgctg      3000
tgcatattgg aggagaaccc tttcttccct gggctcttca tctcacatga catcaccaca      3060
tcacctcgtt ccttggaccc tcagtggtgt cactgctgga tttttctttc ctttggctgg      3120
ccttagggca cacccaggtt gactagcgta gtcatggtat ttagatccac tcacattttc      3180
agtttctgtg tctgtctctt gcctgcttct gacttcgccc agagaaagct tctcttttcac      3240 aagggttctt agatttatgt tcactgagca ccttcttttc tgaggcagtg ttttaccaat      3300
atttattttc ctagtcagtc tcgccttacc tttcttgtta tgcatgtctt tggtcctgac      3360
ccattctctg agtctgtaaa atagaattgc tgtataattt aattacatga aatcctttag      3420
aatcttaaca catcttacac ctgatttaat attttattgt atccaaattg aaccaaccct      3480
atgtgaattt gacagtgatt tctcccaggg atcctagtgt ataaggaata ggacttagta      3540
ttttctattt tttgatatac cacataccag atactgatta tgatggacat ttaacccttt      3600
tttctcatta tgaaagaaag ttaggaatta tttcttccag tagcgccagt gtaacctgaa      3660
agcctttgaa agagtagttt ttgtatagct atctgaaagg aatttctttc caaaatattt      3720
ttccagtgct gacaacaaac acgcagacac accctgcaag gtgagtgtac ggcg            3774

<210> SEQ ID NO 2
<211> LENGTH: 3769
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gggctatccc aggttgcctt ggttcatggc aaatgggacg ttaagagggc agagagaata        60
tgaacagaaa ctgttctaat attggtcatt taatgtgtaa gtattgttct tttttaaacc       120
tccttcattt ttttttccagg aattgctgga cacagtggct tggtgtgtgt ctgaggactg      180
taggccatgg ccctaggttg tggttttagg tctcaggtgc tcttcctggc tgtctccttg      240
```

|  |  |
|---|---|
| cttctttccc atgtcctctt ctttgtttcc agccatttct cccttatgct taagtttggt | 300 |
| gcagcagggt ttggctgctc tcagattcct gcttcctcag atgctgtagt tgtcaggccc | 360 |
| agcgggctgg cagcgggatc aggatctggc taggtttgct ctcactgtgg cagagtaggg | 420 |
| ggaggcgtgg gagagcacgt gtgaccccag gccagctgta gggagcatag gcatggtcac | 480 |
| gtagccttca ggtcctagac tttgtcttct catgagtatg gctgtgtgtg tatggtgaaa | 540 |
| actaggttct acttagccca agaaaatggg cacattttgc atgtggtttc tgtagagaaa | 600 |
| tgcactgggt atctgacata gcctggcagc atgcctccct caggtaggtt agtctcaggc | 660 |
| ggtgaagcac gtgtgtccag caagaacttc atatgtggca taaagtctcc gttctgtgag | 720 |
| gtgctggcaa atcaccacca ccgtcaagag gctgaagtga ttttttgtcta gggaggcagg | 780 |
| aaaggcttcc tggagtcagc agccagtagg tgaaagagta gattggagac cttcttaatc | 840 |
| atcaccgcct cttgtctcaa ggggtgccag gaagctgtgg aggctgaacc catcttatgc | 900 |
| tgccagagag tgggacacca tgagggtcag gtcaaggggt tgtaccttgt ttggtagaga | 960 |
| attagggget cttgaagact ttggatgtgg tcagggagt gtatcattta ggaagagtga | 1020 |
| cccggtgagg acgtggggta gaggaggaca ggtgggaggg agtccaggtg ggagtgagta | 1080 |
| gacccagcag gagtgcaggg cctcgagcca ggatggtggc agggctgtga ggagaggcag | 1140 |
| ccacctgtgt gtctgcggaa gcaggggcaa gagggaagag gccagcagcg tgctgccatc | 1200 |
| acccagcgac tggcgtagat tgtgagagac cattccctgc tcttaggagg ggctgagttt | 1260 |
| tagttttctc ttgttataca ataagcttgg tatttgttta caaaacattt gtaaagctaa | 1320 |
| atcaaggttt gataaggctt ctagtttat ttaagaagta atgttgaaat aaatgtttgt | 1380 |
| ccaattcgct ttgctcattt aaggactttc agtacaaact gcaacaacag gattaggatt | 1440 |
| taaacgtttc tgagatgttt ttactcctca gaatttccca gaatgtgatc tggttttgat | 1500 |
| tttcaagctt gctgacccaa taggttaacc cacaagtttt acgaagacca tctcagtcca | 1560 |
| cttacatcaa ctgcccatgc cacggttaaa gagatcatcg actgatgttt ggcacagctt | 1620 |
| cctccctctt gggtgggcaa gcatttggaa gagaaggctc ctatgggtga gagtggggca | 1680 |
| ccaaagtctt ccctgtccca tccctagct tgagaagccc ttctctaatg tggactttgt | 1740 |
| gccgttagca tcgttactag cttgaagttg accatctgga cgtactttct ggtttagcct | 1800 |
| cacaagtgag caaggagggt tgagagatgt gctgtgagga atgtggggcc ccagctggca | 1860 |
| gcaggctctg ggtcaggggg gcagggacca cgggcatacc tgacagtgag gagggtcta | 1920 |
| gtagggatc agttccctg ttgttctta gaattttctg gatattcttc tttattgatt | 1980 |
| ttgggatgtg aacaatagaa tcaacttcta cttgtagatt gatttaggga gaacttatac | 2040 |
| ctcagatgtt aagtcaccct gtccagaatg tgggatgctt tcctatttgt tcagaacttt | 2100 |
| ttaaattacc tcagaagcac atgaaattta aaggatttta aaaaaaactt aaagattatt | 2160 |
| tcacatagct cttgcacatt tcttgataaa tgaatcctca ggtattcctc tgttttttgtt | 2220 |
| actaatagtt acttcttatg ggttttttt cccctgaaaa tcatttatca aacgtatgtg | 2280 |
| gcttattttc tgaaggatgt ttgataattt tggaagatat gaaagtcttc atattttaca | 2340 |
| aggtttgggg tctcttttaag ctgcatggtt ctcatgtcag ctcccaaagc agaagacggc | 2400 |
| atgttgaaaa atgccgtaga gaagatactt ctttccacc tgttttcaac tcatatcatc | 2460 |
| ttgaatttca gggcaccttt ccatgctcct agtgcttgct atctgtttat tatttttcctt | 2520 |
| cctgaatacc ctgaactcca gcatgttctg ctgtaattct ggcctccctg gcatcttgga | 2580 |
| ctcctgtttc ctttgctctg tcatccccgc ggtcagctcc tgctgcgcag cttctcagct | 2640 |

```
gaagtgcgtt tggagtgcct ggcgtgtctt gctggatctt tgagtattgc ctctggtttc    2700
cttggttcct tctgctgagt tgctcagcgt ctccactccc catttcttgt gtggcccttc    2760
ctgcactcct ctgattcctt ttgtcttccc tggtttcttg ctttggtttc gagtctccac    2820 agaactttig cagctcttct gaagacctgg aagcttttic atcttaattc tcatctcatg    2880
acctcttttc ccttctttga gagctagaac ttcccatggt gaacttctct ttccagaatt    2940
ccatgccttc ttttccctcc cacttacctg ttgtccagga gaggtcagat tgctgtgcat    3000
attggaggag aacccttict tccctgggct cttcatctca catgacatca ccacatcacc    3060
tcgttccttg gaccctcagt ggtgtcactg ctggattttt cttitcctttg gctggcctta    3120 gggcacaccc aggttgacta gcgtagtcat ggtatttaga tccactcaca ttttcagttt    3180
ctgtgtctgt ctcttgcctg cttctgactt cgcccagaga aagcttctct ttcacaaggg    3240
ttcttagatt tatgttcact gagcaccttc ttitictgagg cagtgtttta ccaatattta    3300
ttttcctagt cagtctcgcc ttaccttict tgttatgcat gtctttggtc ctgacccatt    3360
ctctgagtct gtaaaataga attgctgtat aatttaatta catgaaatcc tttagaatct    3420
taacacatct tacacctgat ttaatatttt attgtatcca aattgaacca accctatgtg    3480
aatttgacag tgatttctcc cagggatcct agtgtataag gaataggact tagtattttc    3540
tattttttga tataccacat accagatact gattatgatg gacatttaac ccttttttct    3600
cattatgaaa gaaagttagg aattatttct tccagtagcg ccagtgtaac ctgaaagcct    3660
ttgaaagagt agttttigta tagctatctg aaaggaattt ctticcaaaa tattittcca    3720 gtgctgacaa caaacacgca gacacaccct gcaaggtgag tgtacggcg               3769

<210> SEQ ID NO 3
<211> LENGTH: 9110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ttcgctttct tcccttcctt tctcgccacg ttcgccggct ttccccgtca agctctaaat      60
cgggggctcc ctttagggtt ccgatttagt gctttacggc acctcgaccc caaaaaactt     120
gattagggtg atggttcacg tagtgggcca tcgccctgat agacggtttt tcgccctttg     180
acgttggagt ccacgttctt aatagtggac tcttgttcca aactggaaca acactcaacc     240
ctatctcggt ctattctttt gatttataag ggattttgcc gatttcggcc tattggttaa     300
aaaatgagct gatttaacaa aaatttaacg cgaattttaa caaaatatta acgcttacaa     360
tttaggtggc acttttcggg gaaatgtgcg cggaacccct atttgtttat ttttctaaat     420
acattcaaat atgtatccgc tcatgagaca ataaccctga taaatgcttc aataatattg     480
aaaaaggaag agtatgagta ttcaacattt ccgtgtcgcc cttattccct tttttgcggc     540
attttgcctt cctgtttttg ctcacccaga aacgctggtg aaagtaaaag atgctgaaga     600
tcagttgggt gcacgagtgg gttacatcga actggatctc aacagcggta agatccttga     660
gagttttcgc cccgaagaac gttttccaat gatgagcact tttaaagttc tgctatgtgg     720
cgcggtatta tcccgtattg acgccgggca agagcaactc ggtcgccgca tacactattc     780
tcagaatgac ttggttgagt actcaccagt cacagaaaag catcttacgg atggcatgac     840
agtaagagaa ttatgcagtg ctgccataac catgagtgat aacactgcgg ccaacttact     900
```

```
tctgacaacg atcggaggac cgaaggagct aaccgctttt ttgcacaaca tgggggatca      960
tgtaactcgc cttgatcgtt gggaaccgga gctgaatgaa gccataccaa acgacgagcg     1020
tgacaccacg atgcctgtag caatggcaac aacgttgcgc aaactattaa ctggcgaact     1080
acttactcta gcttcccggc aacaattaat agactggatg gaggcggata agttgcagg     1140 accacttctg cgctcggccc ttccggctgg ctggtttatt gctgataaat ctggagccgg     1200
tgagcgtggg tctcgcggta tcattgcagc actggggcca gatggtaagc cctcccgtat     1260
cgtagttatc tacacgacgg ggagtcaggc aactatggat gaacgaaata gacagatcgc     1320
tgagataggt gcctcactga ttaagcattg gtaactgtca gaccaagttt actcatatat     1380
actttagatt gatttaaaac ttcatttttta atttaaaagg atctaggtga agatcctttt     1440
tgataatctc atgaccaaaa tcccttaacg tgagttttcg ttccactgag cgtcagaccc     1500
cgtagaaaag atcaaaggat cttcttgaga tcctttttttt ctgcgcgtaa tctgctgctt     1560
gcaaacaaaa aaaccaccgc taccagcggt ggtttgtttg ccggatcaag agctaccaac     1620 tcttttccg aaggtaactg gcttcagcag agcgcagata ccaaatactg ttcttctagt     1680
gtagccgtag ttaggccacc acttcaagaa ctctgtagca ccgcctacat acctcgctct     1740
gctaatcctg ttaccagtgg ctgctgccag tggcgataag tcgtgtctta ccgggttgga     1800
ctcaagacga tagttaccgg ataaggcgca gcggtcgggc tgaacggggg gttcgtgcac     1860
acagcccagc ttggagcgaa cgacctacac cgaactgaga tacctacagc gtgagctatg     1920
agaaagcgcc acgcttcccg aagggagaaa ggcggacagg tatccggtaa gcggcagggt     1980
cggaacagga gagcgcacga gggagcttcc agggggaaac gcctggtatc tttatagtcc     2040
tgtcgggttt cgccacctct gacttgagcg tcgatttttg tgatgctcgt caggggggcg     2100
gagcctatgg aaaaacgcca gcaacgcggc ctttttacgg ttcctggcct tttgctggcc     2160
ttttgctcac atgttctttc ctgcgttatc ccctgattct gtggataacc gtattaccgc     2220
ctttgagtga gctgataccg ctcgccgcag ccgaacgacc gagcgcagcg agtcagtgag     2280
cgaggaagcg gaagagcgcc tgatgcggta ttttctcctt acgcatctgt gcggtatttc     2340
acaccgcata gaccagccgc gtaacctggc aaaatcggtt acggttgagt aataaatgga     2400
tgccctgcgt aagcgggtgt gggcggacaa taaagtctta aactgaacaa aatagatcta     2460
aactatgaca ataaagtctt aaactagaca gaatagttgt aaactgaaat cagtccagtt     2520
atgctgtgaa aaagcatact ggacttttgt tatggctaaa gcaaactctt cattttctga     2580
agtgcaaatt gcccgtcgta ttaaagaggg gcgtggccaa gggcatggta agactatat     2640 tcgcggcgtt gtgacaattt accgaacaac tccgcggccg ggaagccgat ctcggcttga     2700
acgaattgtt aggtggcggt acttgggtcg atatcaaagt gcatcacttc ttcccgtatg     2760
cccaactttg tatagagagc cactgcggga tcgtcaccgt aatctgcttg cacgtagatc     2820
acataagcac caagcgcgtt ggcctcatgc ttgaggagat tgatgagcgc ggtggcaatg     2880
ccctgcctcc ggtgctcgcc ggagactgcg agatcataga tatagatctc actacgcggc     2940
tgctcaaact gggcagaac gtaagccgcg agagcgccaa caaccgcttc ttggtcgaag     3000
gcagcaagcg cgatgaatgt cttactacgg agcaagttcc cgaggtaatc ggagtccggc     3060
tgatgttggg agtaggtggc tacgtctccg aactcacgac cgaaaagatc aagagcagcc     3120
cgcatggatt tgacttggtc agggccgagc ctacatgtgc gaatgatgcc catacttgag     3180
ccacctaact ttgttttagg gcgactgccc tgctgcgtaa catcgttgct gctgcgtaac     3240
```

-continued

```
atcgttgctg ctccataaca tcaaacatcg acccacggcg taacgcgctt gctgcttgga    3300
tgcccgaggc atagactgta caaaaaaaca gtcataacaa gccatgaaaa ccgccactgc    3360
gccgttacca ccgctgcgtt cggtcaaggt tctggaccag ttgcgtgagc gcatacgcta    3420
cttgcattac agtttacgaa ccgaacaggc ttatgtcaac tgggttcgtg ccttcatccg    3480
tttccacggt gtgcgtcacc cggcaacctt gggcagcagc gaagtcgagg catttctgtc    3540
ctggctggcg aacgagcgca aggtttcggt ctccacgcat cgtcaggcat ggcggcctt    3600
gctgttcttc tacggcaagg tgctgtgcac ggatctgccc tggcttcagg agatcggaag    3660
acctcggccg tcgcggcgct tgccggtggt gctgaccccg gatgaagtgg ttcgcatcct    3720
cggttttctg gaaggcgagc atcgtttgtt cgcccaggac tctagctata gttctagtgg    3780
ttggctacag cttgcatgcc tgcaggcagc tgcgcgctcg ctcgctcact gaggccgccc    3840
gggcgtcggg cgacctttgg tcgcccggcc tcagtgagcg agcgagcgcg cagagaggga    3900
gtggccaact ccatcactag ggttccttg tagttaatga ttaacccgcc atgctactta    3960
tctacgtagc catgctctag tgaattcgac gccgccatct ctaggcccgc gccggccccc    4020
tcgcacagac ttgtgggaga agctcggcta ctcccctgcc ccggttaatt tgcatataat    4080
atttcctagt aactatagag gcttaatgtg cgataaaaga cagataatct gttcttttta    4140
atactagcta cattttacat gataggcttg gatttctata agagatacaa atactaaatt    4200
attattttaa aaaacagcac aaaaggaaac tcacccctaac tgtaaagtaa ttgtgtgttt    4260
tgagactata aatatcccctt ggagaaaagc cttgtttgcg tttagtgaac cgtcagatgg    4320
taccgtttaa actcgagtga gcgatgctgg ctcgcatggt cgatactgta aagccacaga    4380
tgggtgtcga ccatgcgagc cagcaccgcc tactagagcg gccgccacag cggggagatc    4440
cagacatgat aagatacatt ttttgaattc gggctatccc aggttgcctt ggttcatggc    4500
aaatgggacg ttaagagggc agagagaata tgaacagaaa ctgttctaat attggtcatt    4560
taatgtgtaa gtattgttct ttttttaaacc tccttcattt ttttccagg aattgctgga    4620
cacagtggct tggtgtgtgt ctgaggactg taggccatgg ccctaggttg tggttttagg    4680
tctcaggtgc tcttcctggc tgtctccttg cttctttccc atgtcctctt ctttgtttcc    4740
agccatttct cccttatgct taagtttggt gcagcagggt ttggctgctc tcagattcct    4800
gcttcctcag atgctgtagt tgtcaggccc agcgggctgg cagcgggatc aggatctggc    4860
taggtttgct ctcactgtgg cagagtaggg ggaggcgtgg gagagcacgt gtgacccag    4920
gccagctgta gggagcatag gcatggtcac gtagccttca ggtcctagac tttgtcttct    4980
catgagtatg gctgtgtgtg tatggtgaaa actaggttct acttagccca agaaaatggg    5040
cacattttgc atgtggtttc tgtagagaaa tgcactgggt atctgacata gcctggcagc    5100
atgcctccct caggtaggtt agtctcaggc ggtgaagcac gtgtgtccag caagaacttc    5160
atatgtggca taaagtctcc gttctgtgag gtgctggcaa atcaccacca ccgtcaagag    5220
gctgaagtga ttttgtcta gggaggcagg aaaggcttcc tggagtcagc agccagtagg    5280
tgaaagagta gattggagac cttcttaatc atcaccgcct cttgtctcaa ggggtgccag    5340
gaagctgtga aggctgaacc catcttatgc tgccagagag tggacacca tgagggtcag    5400
gtcaagggt tgtaccttgt ttggtagaga attagggggct cttgaagact tggatgtgg    5460
tcaggggagt gtatcattta ggaagagtga cccggtgagg acgtggggta gaggaggaca    5520
ggtgggaggg agtccaggtg gggagtgagta gacccagcag gagtgcaggg cctcgagcca    5580
ggatggtggc agggctgtga ggagaggcag ccacctgtgt gtctgcggaa gcaggggcaa    5640
```

```
gagggaagag gccagcagcg tgctgccatc acccagcgac tggcgtagat tgtgagagac    5700
cattccctgc tcttaggagg ggctgagttt tagttttctc ttgttataca ataagcttgg    5760
tatttgttta caaaacattt gtaaagctaa atcaaggttt gataaggctt ctagttttat    5820
ttaagaagta atgttgaaat aaatgttgt ccaattcgct ttgctcattt aaggactttc     5880
agtacaaact gcaacaacag gattaggatt taaacgtttc tgagatgttt ttactcctca    5940
gaatttccca gaatgtgatc tggttttgat tttcaagctt gctgacccaa taggttaacc    6000
cacaagtttt acgaagacca tctcagtcca cttacatcaa ctgcccatgc cacggttaaa    6060
gagatcatcg actgatgttt ggcacagctt cctccctctt gggtgggcaa gcatttggaa    6120
gagaaggctc ctatgggtga gagtgggggca ccaaagtctt ccctgtccca tccctagct    6180 tgagaagccc ttctctaatg tggactttgt gccgttagca tcgttactag cttgaagttg    6240
accatctgga cgtactttct ggtttagcct cacaagtgag caaggagggt tgagagatgt    6300
gctgtgagga atgtggggcc ccagctgca gcaggctctg ggtcagggg gcagggacca      6360 cgggcatacc tgacagtgag gagggtctag taggggatca gttcccctgt tgttctttag    6420
aattttctgg atattcttct ttattgattt tgggatgtga acaatagaat caacttctac    6480
ttgtagattg atttagggag aacttatacc tcagatgtta agtcaccctg tccagaatgt    6540
gggatgcttt cctatttgtt cagaactttt taaattacct cagaagcaca tgaaatttaa    6600
aggattttaa aaaaaactta agattatttt cacatagctc ttgcacattt cttgataaat    6660
gaatcctcag gtattcctct gtttttgtta ctaatagtta cttcttatgg gttttttttc    6720
ccctgaaaat catttatcaa acgtatgtgg cttattttct gaaggatgtt tgataatttt    6780
ggaagatatg aaagtcttca tatttttacaa ggtttgaggt ctctttaagc tgcatggttc    6840
tcatgtcagc tcccaaagca gaagacggca tgttgaaaaa tgccgtagag aagatacttc    6900
ttttccacct gttttcaact catatcatct tgaatttcag ggcacctttc catgctccta    6960
gtgcttgcta tctgtttatt attttccttc ctgaatacc tgaactccag catgttctgc      7020
tgtaattctg gcctccctgg catcttggac tcctgtttcc tttgctctgt catccccgcg    7080
gtcagctcct gctgcgcagc ttctcagctg aagtgcgttt ggagtgcctg gcgtgtcttg    7140
ctggatcttt gagtattgcc tctggttttcc ttggttcctt ctgctgagtt gctcagcgtc    7200
tccactcccc atttcttgtg tggccctccc tgcactcctc tgattccttt tgtcttccct    7260
ggtttcttgc tttggtttcg agtctccaca gaacttttgc agctcttctg aagacctgga    7320 agcttttca tcttaattct catctcatga cctcttttcc cttctttgag agctagaact    7380
tcccatggtg aacttctctt tccagaattc catgccttct tttccctccc acttacctgt    7440
tgtccaggag aggtcagatt gctgtgcata ttggaggaga acccttctt ccctgggctc     7500 ttcatctcac atgacatcac cacatcacct cgttccttgg accctcagtg gtgtcactgc    7560 tggattttc tttcctttgg ctggccttag ggcacaccca ggttgactag cgtagtcatg    7620
gtatttagat ccactcacat tttcagtttc tgtgtctgtc tcttgcctgc ttctgacttc    7680
gcccagagaa agcttctctt tcacaagggt tcttagattt atgttcactg agcaccttct    7740
tttctgaggc agtgttttac caatatttat tttcctagtc agtctcgcct tacctttctt    7800
gttatgcatg tctttggtcc tgacccattc tctgagtctg taaaatagaa ttgctgtata    7860
atttaattac atgaaatcct ttagaatctt aacacatctt acacctgatt taatatttta    7920
ttgtatccaa attgaaccaa ccctatgtga atttgacagt gatttctccc agggatccta    7980
```

```
gtgtataagg aataggactt agtatttcct attttttgat ataccacata ccagatactg    8040
attatgatgg acatttaacc cttttttctc attatgaaag aaagttagga attatttctt    8100
ccagtagcgc cagtgtaacc tgaaagcctt tgaaagagta gttttgtat agctatctga    8160 aaggaatttc ttttccaaaat attttttccag tgctgacaac aaacacgcag acacaccctg    8220
caaggtgagt gtacggcgca ctagagcatg gctacgtaga taagtagcat ggcgggttaa    8280
tcattaacta caaggaaccc ctagtgatgg agttggccac tccctctctg cgcgctcgct    8340
cgctcactga ggccgggcga ccaaaggtcg cccgacgccc gggctttgcc cgggcggcct    8400
cagtgagcga gcgagcgcgc agctgcctgc aggtctgaga caataaccct gataaatgct    8460
tcaataatgt aagcttgtcg agaagtacta gaggatcata atcagccata ccacatttgt    8520
agaggtttta cttgctttaa aaacctccc acacctcccc ctgaacctga aacataaaat    8580
gaatgcaatt gttgttgtta acttgtttat tgcagcttat aatggttaca aataaagcaa    8640
tagcatcaca aatttcacaa ataaagcatt ttttttcactg cattctagtt gtggtttgtc    8700
caaactcatc aatgtatctt atcatgtctg gatctgatca ctgatatcgc ctaggagatc    8760
cgaaccagat aagtgaaatc tagttccaaa ctattttgtc attttaatt ttcgtattag    8820 cttacgacgc tacacccagt tccacatctat tttgtcactc ttccctaaat aatccttaaa    8880
aactccattt ccacccctcc cagttcccaa ctattttgtc cgcccacagc ggggcatttt    8940
tcttcctgtt atgttttaa tcaaacatcc tgccaactcc atgtgacaaa ccgtcatctt    9000
cggctacttt ttctctgtca cagaatgaaa attttctgt catctcttcg ttattaatgt    9060
ttgtaattga ctgaatatca acgcttattt gcagcctgaa tggcgaatgg                9110

<210> SEQ ID NO 4
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctcgagtgag cgatgctggc tcgcatggtc gatactgtaa agccacagat gggtgtcgac    60
catgcgagcc agcaccgcct actaga                                          86

<210> SEQ ID NO 5
<211> LENGTH: 311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
cgacgccgcc atctctaggc ccgcgccggc cccctcgcac agacttgtgg gagaagctcg    60
gctactcccc tgccccggtt aatttgcata taatatttcc tagtaactat agaggcttaa    120
tgtgcgataa aagacagata atctgttctt tttaatacta gctacatttt acatgatagg    180
cttggatttc tataagagat acaaatacta aattattatt ttaaaaaaca gcacaaaagg    240
aaactcaccc taactgtaaa gtaattgtgt gttttgagac tataaatatc ccttggagaa    300
aagccttgtt t                                                         311

<210> SEQ ID NO 6
<211> LENGTH: 94
```

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
ctgcgcgctc gctcgctcac tgaggccgcc cgggcgtcgg gcgacctttg gtcgcccggc    60
ctcagtgagc gagcgagcgc gcagagaggg agtg                               94

<210> SEQ ID NO 7
<211> LENGTH: 128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7 aaggaaccccc tagtgatgga gttggccact ccctctctgc gcgctcgctc gctcactgag   60
gccgggcgac caaaggtcgc ccgacgcccg ggctttgccc gggcggcctc agtgagcgag   120
cgagcgcg                                                            128

<210> SEQ ID NO 8
<211> LENGTH: 534
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
ttaggtggcg gtacttgggt cgatatcaaa gtgcatcact tcttcccgta tgcccaactt    60
tgtatagaga gccactgcgg gatcgtcacc gtaatctgct tgcacgtaga tcacataagc   120
accaagcgcg ttggcctcat gcttgaggag attgatgagc gcggtggcaa tgccctgcct   180
ccggtgctcg ccggagactg cgagatcata gatatagatc tcactacgcg gctgctcaaa   240
cttgggcaga acgtaagccg cgagagcgcc aacaaccgct tcttggtcga aggcagcaag   300
cgcgatgaat gtcttactac ggagcaagtt cccgaggtaa tcggagtccg gctgatgttg   360
ggagtaggtg gctacgtctc cgaactcacg accgaaaaga tcaagagcag cccgcatgga   420
tttgacttgg tcagggccga gcctacatgt gcgaatgatg cccatacttg agccacctaa   480
ctttgtttta gggcgactgc cctgctgcgt aacatcgttg ctgctgcgta acat         534

<210> SEQ ID NO 9
<211> LENGTH: 861
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9
atgagtattc aacatttccg tgtcgccctt attcccttttt ttgcggcatt ttgccttcct    60
gtttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtattgacg ccgggcaaga gcaactcggt cgccgcatac actattctca gaatgacttg   300

```
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861

<210> SEQ ID NO 10
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
tgtgggcgga caataaagtc ttaaactgaa caaaatagat ctaaactatg acaataaagt     60
cttaaactag acagaatagt tgtaaactga aatcagtcca gttatgctgt gaaaaagcat    120
actggacttt tgttatggct aaagcaaact cttcattttc tgaagtgcaa attgcccgtc    180
gtattaaaga ggggcgtggc caagggcatg gtaaagacta tattc                   225

<210> SEQ ID NO 11
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
aaccagataa gtgaaatcta gttccaaact attttgtcat ttttaatttt cgtattagct     60
tacgacgcta cacccagttc ccatctattt tgtcactctt ccctaaataa tccttaaaaa    120
ctccatttcc acccctccca gttcccaact attttgtccg cccaca                   166

<210> SEQ ID NO 12
<211> LENGTH: 9111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ttcgctttct tcccttcctt tctcgccacg ttcgccggct ttccccgtca agctctaaat     60
cgggggctcc ctttagggtt ccgatttagt gctttacggc acctcgaccc caaaaaactt    120
gattagggtg atggttcacg tagtgggcca tcgccctgat agacggtttt tcgccctttg    180
acgttggagt ccacgttctt aatagtggac tcttgttcca aactggaaca acactcaacc    240
ctatctcggt ctattctttt gatttataag ggattttgcc gatttcggcc tattggttaa    300
aaaatgagct gatttaacaa aaatttaacg cgaatttaa caaaatatta acgcttacaa    360
```

```
tttaggtggc acttttcggg gaaatgtgcg cggaacccct atttgtttat ttttctaaat    420
acattcaaat atgtatccgc tcatgagaca ataaccctga taaatgcttc aataatattg    480
aaaaggaag agtatgagta ttcaacattt ccgtgtcgcc cttattccct ttttgcggc      540
attttgcctt cctgttttg ctcacccaga aacgctggtg aaagtaaaag atgctgaaga    600
tcagttgggt gcacgagtgg gttacatcga actggatctc aacagcggta agatccttga    660
gagttttcgc cccgaagaac gttttccaat gatgagcact tttaaagttc tgctatgtgg    720
cgcggtatta tcccgtattg acgccgggca agagcaactc ggtcgccgca tacactattc    780
tcagaatgac ttggttgagt actcaccagt cacagaaaag catcttacgg atggcatgac    840
agtaagagaa ttatgcagtg ctgccataac catgagtgat aacactgcgg ccaacttact    900
tctgacaacg atcggaggac cgaaggagct aaccgctttt ttgcacaaca tgggggatca    960
tgtaactcgc cttgatcgtt gggaaccgga gctgaatgaa gccataccaa acgacgagcg    1020
tgacaccacg atgcctgtag caatggcaac aacgttgcgc aaactattaa ctggcgaact    1080
acttactcta gcttcccggc aacaattaat agactggatg gaggcggata agttgcagg    1140
accacttctg cgctcggccc ttccggctgg ctggtttatt gctgataaat ctggagccgg    1200
tgagcgtggg tctcgcggta tcattgcagc actggggcca gatggtaagc cctcccgtat    1260
cgtagttatc tacacgacgg ggagtcaggc aactatggat gaacgaaata gacagatcgc    1320
tgagataggt gcctcactga ttaagcattg gtaactgtca gaccaagttt actcatatat    1380
actttagatt gatttaaaac ttcattttta atttaaaagg atctaggtga agatccttt    1440
tgataatctc atgaccaaaa tcccttaacg tgagttttcg ttccactgag cgtcagaccc    1500
cgtagaaaag atcaaaggat cttcttgaga tcctttttt ctgcgcgtaa tctgctgctt    1560
gcaaacaaaa aaccaccgc taccagcggt ggtttgtttg ccggatcaag agctaccaac    1620
tcttttccg aaggtaactg gcttcagcag agcgcagata ccaaatactg ttcttctagt    1680
gtagccgtag ttaggccacc acttcaagaa ctctgtagca ccgcctacat acctcgctct    1740
gctaatcctg ttaccagtgg ctgctgccag tggcgataag tcgtgtctta ccgggttgga    1800
ctcaagacga tagttaccgg ataaggcgca gcggtcgggc tgaacggggg gttcgtgcac    1860
acagcccagc ttggagcgaa cgacctacac cgaactgaga tacctacagc gtgagctatg    1920
agaaagcgcc acgcttcccg aagggagaaa ggcggacagg tatccggtaa gcggcagggt    1980
cggaacagga gagcgcacga gggagcttcc agggggaaac gcctggtatc tttatagtcc    2040
tgtcgggttt cgccacctct gacttgagcg tcgatttttg tgatgctcgt caggggggcg    2100
gagcctatgg aaaaacgcca gcaacgcggc cttttacgg ttcctggcct tttgctggcc    2160
ttttgctcac atgttctttc ctgcgttatc ccctgattct gtggataacc gtattaccgc    2220
ctttgagtga gctgataccg ctcgccgcag ccgaacgacc gagcgcagcg agtcagtgag    2280
cgaggaagcg gaagagcgcc tgatgcggta ttttctcctt acgcatctgt gcggtatttc    2340
acaccgcata gaccagccgc gtaacctggc aaaatcggtt acggttgagt aataaatgga    2400
tgccctgcgt aagcgggtgt gggcggacaa taaagtctta aactgaacaa atagatcta    2460
aactatgaca ataaagtctt aaactagaca gaatagttgt aaactgaaat cagtccagtt    2520
atgctgtgaa aaagcatact ggactttgt tatggctaaa gcaaactctt cattttctga    2580
agtgcaaatt gcccgtcgta ttaaagaggg gcgtggccaa gggcatggta aagactatat    2640
tcgcggcgtt gtgacaattt accgaacaac tccgcgccg ggaagccgat ctcggcttga    2700
acgaattgtt aggtggcggt acttgggtcg atatcaaagt gcatcacttc ttcccgtatg    2760
```

```
cccaactttg tatagagagc cactgcggga tcgtcaccgt aatctgcttg cacgtagatc   2820
acataagcac caagcgcgtt ggcctcatgc ttgaggagat tgatgagcgc ggtggcaatg   2880
ccctgcctcc ggtgctcgcc ggagactgcg agatcataga tatagatctc actacgcggc   2940
tgctcaaact tgggcagaac gtaagccgcg agagcgccaa caaccgcttc ttggtcgaag   3000
gcagcaagcg cgatgaatgt cttactacgg agcaagttcc cgaggtaatc ggagtccggc   3060
tgatgttggg agtaggtggc tacgtctccg aactcacgac cgaaaagatc aagagcagcc   3120
cgcatggatt tgacttggtc agggccgagc ctacatgtgc gaatgatgcc catacttgag   3180
ccacctaact ttgttttagg gcgactgccc tgctgcgtaa catcgttgct gctgcgtaac   3240
atcgttgctg ctccataaca tcaaacatcg acccacggcg taacgcgctt gctgcttgga   3300
tgcccgaggc atagactgta caaaaaaaca gtcataacaa gccatgaaaa ccgccactgc   3360
gccgttacca ccgctgcgtt cggtcaaggt tctggaccag ttgcgtgagc gcatacgcta   3420
cttgcattac agtttacgaa ccgaacaggc ttatgtcaac tgggttcgtg ccttcatccg   3480
tttccacggt gtgcgtcacc cggcaacctt gggcagcagc gaagtcgagg catttctgtc   3540
ctggctggcg aacgagcgca aggtttcggt ctccacgcat cgtcaggcat ggcggcctt   3600 gctgttcttc tacggcaagg tgctgtgcac ggatctgccc tggcttcagg agatcggaag   3660
acctcggccg tcgcggcgct tgccggtggt gctgaccccg gatgaagtgg ttcgcatcct   3720
cggttttctg gaaggcgagc atcgtttgtt cgcccaggac tctagctata gttctagtgg   3780
ttggctacag cttgcatgcc tgcaggcagc tgcgcgctcg ctcgctcact gaggccgccc   3840
gggcgtcggg cgacctttgg tcgcccggcc tcagtgagcg agcgagcgcg cagagaggga   3900
gtggccaact ccatcactag gggttccttg tagttaatga ttaacccgcc atgctactta   3960
tctacgtagc catgctctag tgaattcgac gccgccatct ctaggcccgc gccggccccc   4020
tcgcacagac ttgtgggaga agctcggcta ctcccctgcc ccggttaatt tgcatataat   4080
atttcctagt aactatagag gcttaatgtg cgataaaaga cagataatct gttctttttta   4140 atactagcta catttacat gataggcttg gatttctata agagatacaa atactaaatt   4200
attattttaa aaacagcac aaaaggaaac tcaccctaac tgtaaagtaa ttgtgtgttt   4260
tgagactata aatatcccct tggagaaaagc cttgtttgcg tttagtgaac cgtcagatgg   4320
taccgtttaa actcgagtga gcgatgctgg ctcgcatggt cgatactgta aagccacaga   4380
tgggtgtcga ccatgcgagc cagcaccgcc tactagagcg gccgccacag cggggagatc   4440
cagacatgat aagatacatt ttttgaattc gggctatccc aggttgcctt ggttcatggc   4500
aaatgggacg ttaagagggc agagagaata tgaacagaaa ctgttctaat attggtcatt   4560
taatgtgtaa gtattgttct tttttaaacc tccttcattt tttttccagg aattgctgga   4620
cacagtggct tggtgtgtgt ctgaggactg taggccatgg ccctaggttg tggttttagg   4680
tctcaggtgc tcttcctggc tgtctccttg cttctttccc atgtcctctt ctttgtttcc   4740
agccatttct cccttatgct taagtttggt gcagcagggt ttggctgctc tcagattcct   4800
gcttcctcag atgctgtagt tgtcaggccc agcgggctgg cagcgggatc aggatctggc   4860
taggtttgct ctcactgtgg cagagtaggg ggaggcgtgg gagagcacgt gtgacccag   4920 gccagctgta gggagcatag gcatggtcac gtagccttca ggtcctagac tttgtcttct   4980
catgagtatg gctgtgtgtg tatggtgaaa actaggttct acttagccca agaaaatggg   5040
cacattttgc atgtggtttc tgtagagaaa tgcactgggt atctgacata gcctggcagc   5100
```

-continued

```
atgcctccct caggtaggtt agtctcaggc ggtgaagcac gtgtgtccag caagaacttc    5160
atatgtggca taaagtctcc gttctgtgag gtgctggcaa atcaccacca ccgtcaagag    5220
gctgaagtga tttttgtcta gggaggcagg aaaggcttcc tggagtcagc agccagtagg    5280
tgaaagagta gattggagac cttcttaatc atcaccgcct cttgtctcaa ggggtgccag    5340
gaagctgtgg aggctgaacc catcttatgc tgccagagag tgggacacca tgagggtcag    5400
gtcaaggggt tgtaccttgt ttggtagaga attaggggct cttgaagact ttggatgtgg    5460
tcagggagt gtatcattta ggaagagtga cccggtgagg acgtggggta gaggaggaca    5520
ggtgggaggg agtccaggtg ggagtgagta gacccagcag gagtgcaggg cctcgagcca    5580
ggatggtggc agggctgtga ggagaggcag ccacctgtgt gtctgcggaa gcaggggcaa    5640
gagggaagag gccagcagcg tgctgccatc acccagcgac tggcgtagat tgtgagagac    5700
cattccctgc tcttaggagg ggctgagttt tagttttctc ttgttataca ataagcttgg    5760
tatttgttta caaaacattt gtaaagctaa atcaaggttt gataaggctt ctagttttat    5820
ttaagaagta atgttgaaat aaatgtttgt ccaattcgct ttgctcattt aaggactttc    5880
agtacaaact gcaacaacag gattaggatt taaacgtttc tgagatgttt ttactcctca    5940
gaatttccca gaatgtgatc tggttttgat tttcaagctt gctgacccaa taggttaacc    6000
cacaagtttt acgaagacca tctcagtcca cttacatcaa ctgcccatgc cacggttaaa    6060
gagatcatcg actgatgttt ggcacagctt cctccctctt gggtgggcaa gcatttggaa    6120
gagaaggctc ctatgggtga gagtgggggca ccaaagtctt ccctgtccca tccctagct    6180
tgagaagccc ttctctaatg tggactttgt gccgttagca tcgttactag cttgaagttg    6240
accatctgga cgtactttct ggtttagcct cacaagtgag caaggagggt tgagagatgt    6300
gctgtgagga atgtggggcc ccagctggca gcaggctctg ggtcagggg gcagggacca    6360
cgggcatacc tgacagtgag gaggggtcta gtagggatc agttcccctg ttgttcttta    6420
gaattttctg gatattcttc tttattgatt ttgggatgtg aacaatagaa tcaacttcta    6480
cttgtagatt gatttaggga gaacttatac ctcagatgtt aagtcaccct gtccagaatg    6540
tgggatgctt tcctatttgt tcagaacttt ttaaattacc tcagaagcac atgaaattta    6600
aaggatttta aaaaaaactt aaagattatt tcacatagct cttgcacatt tcttgataaa    6660
tgaatcctca ggtattcctc tgttttgtt actaatagtt acttcttatg ggttttttt    6720
cccctgaaaa tcatttatca aacgtatgtg gcttattttc tgaaggatgt tgataattt    6780
tggaagatat gaaagtcttc atattttaca aggtttgggg tctctttaag ctgcatggtt    6840
ctcatgtcag ctcccaaagc agaagacggc atgttgaaaa atgccgtaga aagatactt    6900
cttttccacc tgttttcaac tcatatcatc ttgaatttca gggcacctttt ccatgctcct    6960
agtgcttgct atctgtttat tattttcctt cctgaatacc ctgaactcca gcatgttctg    7020
ctgtaattct ggcctccctg gcatcttgga ctcctgtttc ctttgctctg tcatccccgc    7080
ggtcagctcc tgctgcgcag cttctcagct gaagtgcgtt tggagtgcct ggcgtgtctt    7140
gctggatctt tgagtattgc ctctggtttc cttggttcct tctgctgagt tgctcagcgt    7200
ctccactccc catttcttgt gtggcccttc ctgcactcct ctgattcctt ttgtcttccc    7260
tggtttcttg ctttggtttc gagtctccac agaacttttg cagctcttct gaagacctgg    7320
aagctttttc atcttaattc tcatctcatg acctcttttc ccttctttga gagctagaac    7380
ttcccatggt gaacttctct ttccagaatt ccatgccttc ttttccctcc cacttacctg    7440
ttgtccagga gaggtcagat tgctgtgcat attggaggag aacccttcct tccctgggct    7500
```

```
cttcatctca catgacatca ccacatcacc tcgttccttg gaccctcagt ggtgtcactg    7560
ctggattttt ctttcctttg gctggcctta gggcacaccc aggttgacta gcgtagtcat    7620
ggtatttaga tccactcaca ttttcagttt ctgtgtctgt ctcttgcctg cttctgactt    7680
cgcccagaga aagcttctct ttcacaaggg ttcttagatt tatgttcact gagcaccttc    7740
ttttctgagg cagtgtttta ccaatattta ttttcctagt cagtctcgcc ttacctttct    7800
tgttatgcat gtctttggtc ctgacccatt ctctgagtct gtaaaataga attgctgtat    7860
aatttaatta catgaaatcc tttagaatct taacacatct tacacctgat ttaatatttt    7920
attgtatcca aattgaacca accctatgtg aatttgacag tgatttctcc cagggatcct    7980
agtgtataag gataggact  tagtattttc tattttttga tataccacat accagatact     8040
gattatgatg gacatttaac ccttttttct cattatgaaa gaagttagg  aattatttct     8100 tccagtagcg ccagtgtaac ctgaaagcct ttgaaagagt agttttgta  tagctatctg     8160 aaaggaattt ctttccaaaa tattttccca gtgctgacaa caaacacgca gacacaccct    8220
gcaaggtgag tgtacggcgc actagagcat ggctacgtag ataagtagca tggcgggtta    8280
atcattaact acaaggaacc cctagtgatg gagttggcca ctccctctct gcgcgctcgc    8340
tcgctcactg aggccgggcg accaaaggtc gcccgacgcc cgggctttgc ccgggcggcc    8400
tcagtgagcg agcgagcgcg cagctgcctg caggtctgag acaataaccc tgataaatgc    8460
ttcaataatg taagcttgtc gagaagtact agaggatcat aatcagccat accacatttg    8520
tagaggtttt acttgcttta aaaaacctcc cacacctccc cctgaacctg aaacataaaa    8580
tgaatgcaat tgttgttgtt aacttgttta ttgcagctta taatggttac aaataaagca    8640
atagcatcac aaatttcaca aataaagcat tttttcact  gcattctagt tgtggtttgt     8700
ccaaactcat caatgtatct tatcatgtct ggatctgatc actgatatcg cctaggagat    8760
ccgaaccaga taagtgaaat ctagttccaa actattttgt catttttaat tttcgtatta    8820
gcttacgacg ctacacccag ttcccatcta ttttgtcact cttccctaaa taatccttaa    8880
aaactccatt tccaccccctc ccagttccca actattttgt ccgcccacag cggggcattt   8940
ttcttcctgt tatgttttta atcaaacatc ctgccaactc catgtgacaa accgtcatct    9000
tcggctactt tttctctgtc acagaatgaa aattttctg tcatctcttc  gttattaatg     9060
tttgtaattg actgaatatc aacgcttatt tgcagcctga atggcgaatg g              9111
```